US011890105B1

(12) United States Patent
Nguyen et al.

(10) Patent No.: US 11,890,105 B1
(45) Date of Patent: Feb. 6, 2024

(54) COMPUTE SYSTEM WITH PSORIASIS DIAGNOSTIC MECHANISM AND METHOD OF OPERATION THEREOF

(71) Applicant: BelleTorus Corporation, Cambridge, MA (US)

(72) Inventors: Tien Dung Nguyen, Toulouse (FR); Léa Mathilde Gazeau, Toulouse (FR); Matthew Gregory Gloss, San Mateo, CA (US); Thomas Hustache-Marmou, Toulouse (FR); Kavita Mariwalla, Oyster Bay, NY (US); Emily Kathryn McAnelly, Alexandria, VA (US); Megan M. Morbitzer, Westerville, OH (US); Duong Thuy Nguyen, Hanoi (VN); Hoang-Phuong Nguyen, Toulouse (FR); Nga Thi Thuy Nguyen, Toulouse (FR); Thang Duc Nguyen, Toulouse (FR); Thi Thu Hang Nguyen, Toulouse (FR); Clifford Perlis, Penn Valley, PA (US); Christopher C. Szajna, Keswick, VA (US); Jonathan Wolfe, Plymouth Meeting, PA (US)

(73) Assignee: BelleTorus Corporation, Cambridge, MA (US)

( * ) Notice: Subject to any disclaimer, the term of this patent is extended or adjusted under 35 U.S.C. 154(b) by 0 days.

(21) Appl. No.: 17/893,632

(22) Filed: Aug. 23, 2022

(51) Int. Cl.
*A61B 5/00* (2006.01)
*G06T 7/00* (2017.01)
(Continued)

(52) U.S. Cl.
CPC ............ *A61B 5/441* (2013.01); *G06T 7/0012* (2013.01); *G06T 7/10* (2017.01); *G16H 30/40* (2018.01);
(Continued)

(58) Field of Classification Search
CPC ... A61B 5/441; A61B 2576/02; G06T 7/0012; G06T 7/10; G06T 2207/20132; G06T 2207/30088; G16H 30/40
See application file for complete search history.

(56) References Cited

U.S. PATENT DOCUMENTS

| 7,983,718 B1 * | 7/2011 | Roka ................. H04M 1/27475 348/14.02 |
| 11,551,059 B1 * | 1/2023 | Yang ....................... G06F 17/18 |

(Continued)

OTHER PUBLICATIONS

N. Meienberger, F. Anzengruber, L. Amruthalingam, R. Christen,3 T. Koller, J.T. Maul, M Pouly, V. Djamei, and A.A. Navarini, article called "Observer-Independent Assessment of Psoriasis-Affected Area Using Machine Learning", DOI: 10.1111/jdv.16002, JEADV 2020, 34, pp. 1362-1368, @ 2019 European Academy of Dermatology and Venereology.

(Continued)

*Primary Examiner* — Eric F Winakur
*Assistant Examiner* — Abid A Mustansir
(74) *Attorney, Agent, or Firm* — Perspectives Law Group, Corp.

(57) ABSTRACT

A method of operation of a compute system includes: generating a skin segmentation including a non-skin region and a skin prediction based on a patient image; generating a body part segmentation based on the patient image; generating a cropped image based on the skin segmentation and the body part segmentation with the cropped image includes the non-skin region based on the skin prediction; generating a psoriasis segmentation based on the cropped image and the skin prediction; generating intermediate scores for erythema, induration, desquamation for the cropped image; and generating a full body PASI score based a psoriasis segmentation and the intermediate scores on the for displaying on a device to assist in diagnosis.

20 Claims, 14 Drawing Sheets
(4 of 14 Drawing Sheet(s) Filed in Color)

(51) Int. Cl.
*G16H 30/40* (2018.01)
*G06T 7/10* (2017.01)

(52) U.S. Cl.
CPC . *A61B 2576/02* (2013.01); *G06T 2207/20132* (2013.01); *G06T 2207/30088* (2013.01)

(56) References Cited

U.S. PATENT DOCUMENTS

| | | | | |
|---|---|---|---|---|
| 2012/0308096 | A1* | 12/2012 | Mohamad Hani | G06T 7/0012 382/128 |
| 2018/0322629 | A1* | 11/2018 | Hu | G06T 7/75 |
| 2021/0275085 | A1* | 9/2021 | George | G06T 7/0012 |

OTHER PUBLICATIONS

Olaf Ronneberger, Philipp Fischer, and Thomas Brox, "U-Net: Convolutional Networks for Biomedical Image Segmentation", Computer Science Department and BIOSS Centre for Biological Signalling Studies, University of Freiburg, Germany, arXiv: 1505.04597v1 [cs.CV], May 18, 2015, 8 pages.

Mingxing Tan and Quoc V. Le, "EfficientNet: Rethinking Model Scaling for Convolutional Neural Networks", arXiv:1905.11947v5 [cs.LG] Sep. 11, 2020, 11 pages.

\* cited by examiner

COMPUTE SYSTEM WITH PSORIASIS DIAGNOSTIC MECHANISM AND METHOD OF OPERATION THEREOF

TECHNICAL FIELD

An embodiment of the present invention relates generally to a compute system, and more particularly to a system with a psoriasis diagnostic mechanism.

BACKGROUND

Psoriasis is an immune-mediated disease (a disease with an unclear cause that is characterized by inflammation caused by dysfunction of the immune system) that causes inflammation in the body. There can be visible signs of the inflammation on the skin. Inflammation caused by psoriasis can impact other organs and tissues in the body. People with psoriasis may also experience other health conditions.

Thus, a need still remains for a compute system with a psoriasis diagnostic mechanism to provide an objective psoriasis score to provide for a reproducible score to assist healthcare professionals and payers in the diagnosis of psoriasis. In view of the ever-increasing commercial competitive pressures, along with growing healthcare needs, healthcare expectations, and the diminishing opportunities for meaningful product differentiation in the marketplace, it is increasingly critical that answers be found to these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

An embodiment of the present invention provides a method of operation of a compute system including: generating a skin segmentation including a non-skin region and a skin prediction based on a patient image; generating a body part segmentation based on the patient image; generating a cropped image based on the skin segmentation and the body part segmentation with the cropped image includes the non-skin region based on the skin prediction; generating a psoriasis segmentation based on the cropped image and the skin prediction; generating intermediate scores for erythema, induration, desquamation for the cropped image; and generating a full body PASI score based a psoriasis segmentation and the intermediate scores on the for displaying on a device to assist in diagnosis.

An embodiment of the present invention provides a compute system, including a control circuit (1612), including a processor, configured to generate a skin segmentation (204) including a non-skin region (224) and a skin prediction (225) based on a patient image (114), generate a body part segmentation (208) based on the patient image (114), generate a cropped image (226) based on the skin segmentation (204) and the body part segmentation (208) with the cropped image (226) includes the non-skin region (224) based on the skin prediction (225), generate a psoriasis segmentation (206) based on the cropped image (226) and the skin prediction (225), generate intermediate scores (210) for erythema, induration, desquamation for the cropped image (226), and generate a full body PASI score (116) based a psoriasis segmentation (206) and the intermediate scores (210) on the for displaying on a device (102) to assist in diagnosis.

An embodiment of the present invention provides a non-transitory computer readable medium including instructions for a compute system, including: generating a skin segmentation including a non-skin region and a skin prediction based on a patient image; generating a body part segmentation based on the patient image; generating a cropped image based on the skin segmentation and the body part segmentation with the cropped image includes the non-skin region based on the skin prediction; generating a psoriasis segmentation based on the cropped image and the skin prediction; generating intermediate scores for erythema, induration, desquamation for the cropped image; and generating a full body PASI score based a psoriasis segmentation and the intermediate scores on the for displaying on a device to assist in diagnosis.

Certain embodiments of the invention have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
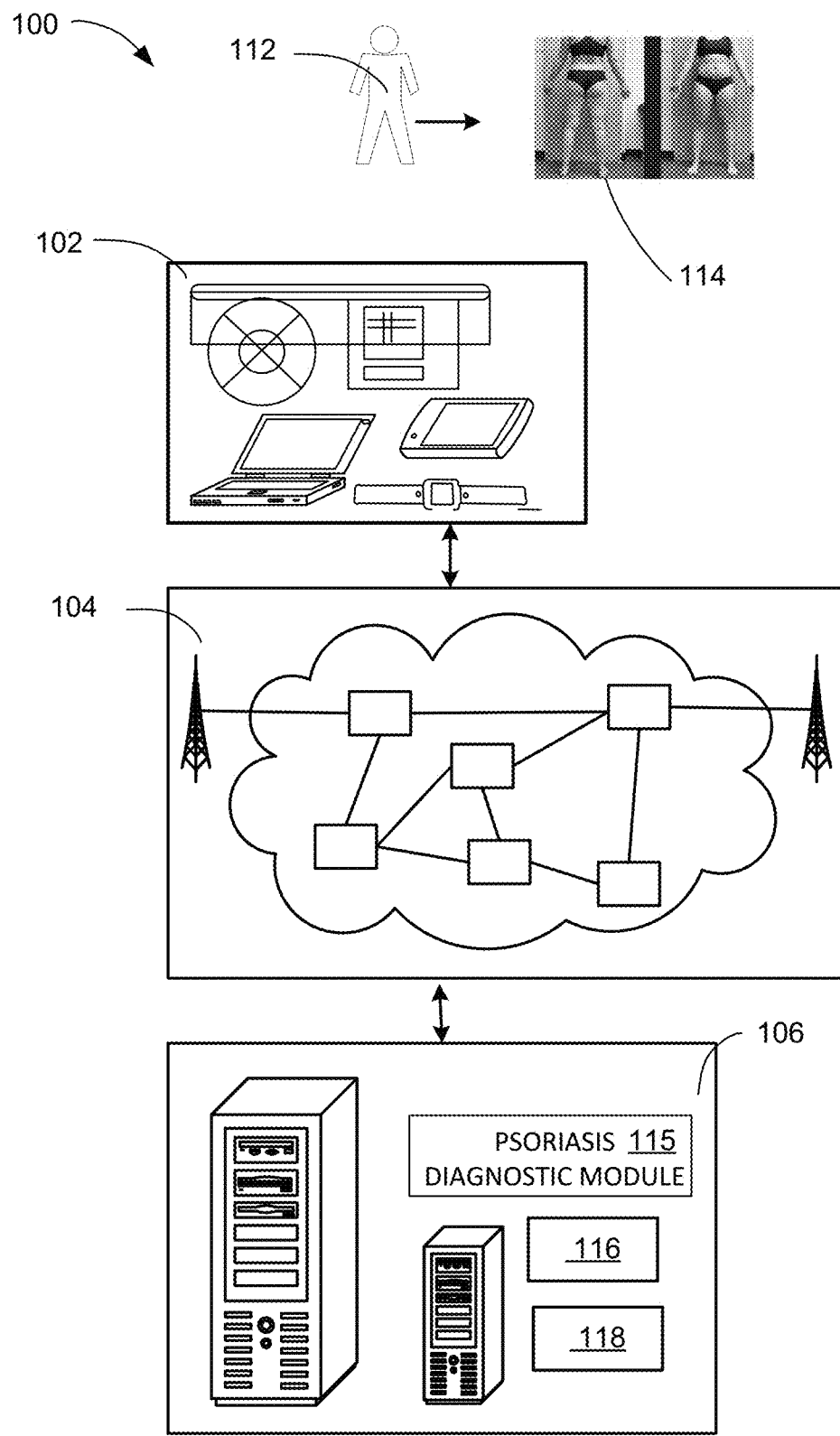
FIG. 1 is an example of a system architecture diagram of a compute system with a psoriasis diagnostic mechanism in an embodiment of the present invention.

Psoriasis are visible signs of the inflammation due to the overactive immune system speeds up skin cell growth. Normal skin cells completely grow and shed (fall off) in a month. With psoriasis, skin cells do this in only three or four days. Instead of shedding, the skin cells pile up on the surface of the skin. Some people report that psoriasis plaques itch, burn and sting. Plaques and scales can appear on any part of the body. There may be visible signs of the inflammation such as raised plaques (plaques may look different for different skin types) and scales on the skin. Plaques can be a few small patches or can affect large areas. Psoriasis plaques and scales can form in more than one location on the body at a time.

Psoriasis can lead to other health conditions impacting other organs or tissues. Psoriasis can also lead to develop psoriatic arthritis. Signs of psoriatic arthritis include swelling, stiffness and pain in the joints and areas surrounding the joints. Psoriatic arthritis often goes undiagnosed, particularly in its milder forms. However, it is important to treat psoriatic arthritis early on to help avoid permanent joint damage as well as other potentially severe health conditions.

Psoriasis symptoms can start between ages 15 and 25, but can start at any age. Men, women, and children of all skin colors can get psoriasis. There are different types of psoriasis. A person can be inflicted with more than one type of psoriasis at one time and more than one type in a lifetime. Treatments may vary depending on the type and location of the psoriasis.

For purposes of treatment planning, patients can be grouped into mild (or limited) disease and extensive (moderate to severe) disease categories. Mild skin disease can often be managed with topical agents, while patients with moderate to severe disease may need phototherapy or systemic therapy. The location of the disease and the presence of psoriatic arthritis also affect the choice of therapy. Widespread pustular disease requires aggressive treatment, which may include hospitalization.

Moderate to severe psoriasis is typically involve of more than 5 to 10 percent of the body surface area (BSA) (the entire palmar surface, including fingers, of one hand is approximately 1 percent of the BSA) or involvement of the face, palm or sole, or disease that is otherwise disabling. Patients with more than 5 percent BSA affected are generally candidates for phototherapy or systemic therapy, since application of topical agents to a large area is not usually practical or acceptable for most patients. Attempts to treat extensive disease with topical agents alone are often met with failure, can add cost, and lead to frustration in the patient-clinician relationship. However, topical agents are useful adjuncts for resistant, localized lesions in patients who are getting phototherapy or systemic agents for extensive involvement.

Established therapies, such as methotrexate and phototherapy, can be employed for the management of moderate to severe plaque psoriasis. The management of patients with extensive or recalcitrant disease is a challenge even for experienced dermatologists. Severe psoriasis requires phototherapy or systemic therapies. Patients with severe psoriasis generally require care by a dermatologist.

The Psoriasis Area Severity Index (PASO is a quantitative value from the structured visual observation of an individual patient's psoriasis lesions and body surface area (BSA). PASI is the gold standard relied on by patients, clinicians, and health insurance payers to assess patient reported and clinician observed psoriatic treatment outcomes. PASI is inherently subjective, such as including inter- and intra-observer reporting variability and reporting oddities. PASI's non-standardized implementation leads to unfair access to dermatology care, especially in rural and low-resource communities. As a result, many patients miss needed diagnoses and treatment.

PASI offers a computational structure to calculate a PASI score, and includes applicable bases to assess lesion severity and to estimate BSA impacted by psoriasis. A PASI score serves to evaluate the occurrence, progression, and treatment of plaque psoriasis (psoriasis or psoriasis lesions).

Patient-centric psoriasis skin healthcare requires standardized and reproducible PASI scoring for effective treatment pathways, unbiased algorithmic design to account for darker skin tones, and ease-of-access to ongoing diagnosis and treatment tracking.

Similarly, calculating PASI scores is inherently subjective. Actual calculated PASI scoring results also show evidence of inter- and intra-observer reporting variability and reporting oddities, e.g., on its scale of 0 to 72, PASI<10 defines mild psoriasis, PASI>10 defines severe psoriasis, 100=no disease, a score of 100 is the same as a score of 50, scores tend to be low and grouped together (confirm again), and a 75% reduction in calculated PASI score determines treatment effectiveness.

Patient-centric psoriasis skin healthcare requires standardized and reproducible PASI scoring for many essential reasons, including, importantly, correct payer reimbursement decisions to allow access to proper treatment. PASI's current instantiation is imprecise. Current PASI does not model comprehensive and diverse data necessary to transform individual patient circumstances into a precise predictive assessment of psoriatic and co-occurring disease conditions.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present invention.

In the following description, numerous specific details are given to provide a thorough understanding of the invention. However, it will be apparent that the invention may be practiced without these specific details. In order to avoid obscuring an embodiment of the present invention, some well-known circuits, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation. The embodiments of various components as a matter of descriptive convenience and are not intended to have any other significance or provide limitations for an embodiment of the present invention.

One skilled in the art would appreciate that the format with which navigation information is expressed is not critical to some embodiments of the invention. For example, in some embodiments, location information is presented in the format of (X, Y, Z); where X and Y and Z are three coordinates, such as latitude, longitude, and elevation that define the geographic location, i.e., a position of a device capturing images.

The term "module" or "unit" or "circuit" referred to herein can include or be implemented as or include software running on specialized hardware, hardware, or a combination thereof in the present invention in accordance with the context in which the term is used. For example, the software can be machine code, firmware, embedded code, and application software. The software can also include a function, a call to a function, a code block, or a combination thereof.

Also, for example, the hardware can be gates, circuitry, processor, computer, integrated circuit, integrated circuit cores, memory devices, a pressure sensor, an inertial sensor, a microelectromechanical system (MEMS), passive devices, physical non-transitory memory medium including instructions for performing the software function, a portion therein, or a combination thereof to control one or more of the hardware units or circuits. Further, if a "module" or "unit" or a "circuit" is written in the claims section below, the "unit" or the "circuit" is deemed to include hardware circuitry for the purposes and the scope of the claims.

The module, units, or circuits in the following description of the embodiments can be coupled or attached to one another as described or as shown. The coupling or attachment can be direct or indirect without or with intervening items between coupled or attached modules or units or circuits. The coupling or attachment can be by physical contact or by communication between modules or units or circuits, such as wireless communication.

It is also understood that the nouns or elements in the embodiments can be described as a singular instance. It is understood that the usage of singular is not limited to singular but the singular usage can be applicable to multiple instances for any particular noun or element in the application. The numerous instances can be the same or similar or can be different.

Referring now to FIG. 1, therein is shown an example of a system architecture diagram of a compute system 100 with a psoriasis diagnostic mechanism in an embodiment of the present invention. Embodiments of the compute system 100 provide standardized and objective psoriasis scoring to provide for a reproducible precise PASI calculation, especially since healthcare payers rely on PASI calculations to reach payment reimbursement decisions and to enable patients to have access proper treatments.

The compute system 100 can include a first device 102, such as a client or a server, connected to a second device 106, such as a client or server. The first device 102 can communicate with the second device 106 through a network 104, such as a wireless or wired network.

For example, the first device 102 can be of any of a variety of computing devices, such as a smart phone, a tablet, a cellular phone, personal digital assistant, a notebook computer, a wearable device, internet of things (IoT) device, or other multi-functional device. Also, for example, the first device 102 can be included in a device or a sub-system.

The first device 102 can couple, either directly or indirectly, to the network 104 to communicate with the second device 106 or can be a stand-alone device. The first device 102 can further be separate form or incorporated with a vehicle, such as a car, truck, bus, motorcycle, or a drone.

For illustrative purposes, the compute system 100 is described with the first device 102 as a mobile device, although it is understood that the first device 102 can be different types of devices. For example, the first device 102 can also be a non-mobile computing device, such as a server, a server farm, cloud computing, or a desktop computer.

The second device 106 can be any of a variety of centralized or decentralized computing devices. For example, the second device 106 can be a computer, grid computing resources, a virtualized computer resource, cloud computing resource, routers, switches, peer-to-peer distributed computing devices, or a combination thereof.

The second device 106 can be centralized in a single room, distributed across different rooms, distributed across different geographical locations, embedded within a telecommunications network. The second device 106 can couple with the network 104 to communicate with the first device 102. The second device 106 can also be a client type device as described for the first device 102.

For illustrative purposes, the compute system 100 is described with the second device 106 as a non-mobile computing device, although it is understood that the second device 106 can be different types of computing devices. For example, the second device 106 can also be a mobile computing device, such as notebook computer, another client device, a wearable device, or a different type of client device.

Also, for illustrative purposes, the compute system 100 is described with the second device 106 as a computing device, although it is understood that the second device 106 can be different types of devices. Also, for illustrative purposes, the compute system 100 is shown with the second device 106 and the first device 102 as endpoints of the network 104, although it is understood that the compute system 100 can include a different partition between the first device 102, the second device 106, and the network 104. For example, the first device 102, the second device 106, or a combination thereof can also function as part of the network 104.

The network 104 can span and represent a variety of networks. For example, the network 104 can include wireless communication, wired communication, optical, ultrasonic, or the combination thereof. Satellite communication, cellular communication, Bluetooth, Infrared Data Association standard (IrDA), wireless fidelity (WiFi), and worldwide interoperability for microwave access (WiMAX) are examples of wireless communication that can be included in the communication path. Ethernet, digital subscriber line (DSL), fiber to the home (FTTH), and plain old telephone service (POTS) are examples of wired communication that can be included in the network 104. Further, the network 104 can traverse a number of network topologies and distances. For example, the network 104 can include direct connection, personal area network (PAN), local area network (LAN), metropolitan area network (MAN), wide area network (WAN), or a combination thereof.

Returning to the description standardized and objective psoriasis scoring of the embodiments of the compute system 100, as an example, the compute system 100 provide functions to various users 112, including patients and clinicians. The compute system 100 can provide functions to the users 112 in a number of ways.

For example, the compute system 100 can provide the functions for the users 112 with the first device 102, the second device 106, distributed between these two devices, or a combination thereof. Also as examples, the compute system 100 can provide a mobile applications for the patients, the clinicians, or a combination thereof. Further as an example, the compute system 100 can provide the functions via a web-browser based applications or a software to be executed on the first device 102, the second device 106, distributed between these two devices, or a combination thereof.

In one embodiment as an example, patient images 114 are taken and uploaded by the patient and reviewed by the clinician. In this embodiment, a patient launches the psoriasis diagnostic mechanism via the mobile application and logs into the patient's account. The patient can be prompted to upload or take body images as the patient images 114. The compute system 100 can guide a patient on photo guidelines for the patient images 114 and accepts or rejects the patient images 114 for retake based on a pre-specified criteria, e.g., distance, quality, blur, or a combination thereof. The compute system 100 can also provide guides for a patient on capturing videos as opposed to still photos. The patient images 114 can be selected from the video.

Once the patient images 114, as required for analysis, are successfully uploaded, the compute system 100 can send or load the patient images 114 to a psoriasis diagnostic module 115 for analysis. The psoriasis diagnostic module 115 will be described later. For brevity and clarity and as an example, the psoriasis diagnostic module 115 is shown in FIG. 1 as being executed in the second device 106 although it is understood that portions can operate on the first device 102, such as the mobile app or the web-browser based application, can operate completely on the first device 102, or a combination thereof. As a further example, the psoriasis diagnostic module 115 can implemented in software running on specialized hardware, full hardware, or a combination thereof.

Based on analysis results, the compute system 100 can display information to the patient including a recommendation based on the patient images 114, uploaded, for the patient to schedule a visit with your primary care physician or with a specialist based on a full body PASI score 116, which may or may not be visible or displayed to the patient.

If the psoriasis diagnostic module 115 provides the full body PASI score 116 below a pre-specified threshold 118, the compute system 100 can display a message that based on the patient images 114, uploaded, the patient may not need a visit with your primary care physician or with other specialist. The compute system 100 can provide a function allowing the patient to schedule a visit with the clinician.

Continuing the example, the compute system 100 can provide a function that allow the clinician to access the patient images 114 uploaded by the patient and a full body PASI score 116, such as with the web-based dashboard from the psoriasis diagnostic mechanism. The compute system 100 allows the clinician to make edits to annotations determined by the psoriasis diagnostic module 115 and the scores (if necessary) and saves the results. The clinician can utilize the full body PASI score 116 to make the diagnostic decision and takes necessary treatment steps (if applicable).

In a further embodiment as an example, the compute system 100 can allow a patient to schedule a visit with a primary care physician or with a specialist. A clinician can launch the psoriasis diagnostic mechanism, such as a mobile application and logs in. The compute system 100 can be prompted to upload or take the patient images 114 of the patient's body or body parts to be analyzed by the psoriasis diagnostic module 115.

The compute system 100 can provide guidance to the clinician on the photo guidelines. The compute system 100 can accept or reject images for retake based on a pre-specified criteria, such as distance, quality, blur, or a combination thereof. Once the patient images 114 are successfully uploaded, the compute system 100 and send or load the patient images 114 to the psoriasis diagnostic module 115 for analysis.

Continuing the example, the compute system 100 can similarly provide a function that allow the clinician to access the patient images 114 uploaded by the patient and the full body PASI score 116, such as with the web-based dashboard from the psoriasis diagnostic mechanism. The compute system 100 allows the clinician to make edits to annotations determined by the psoriasis diagnostic module 115 and the scores (if necessary) and saves the results. The clinician can utilize the full body PASI score 116 to make the diagnostic decision and takes necessary treatment steps (if applicable).

Figure 2:
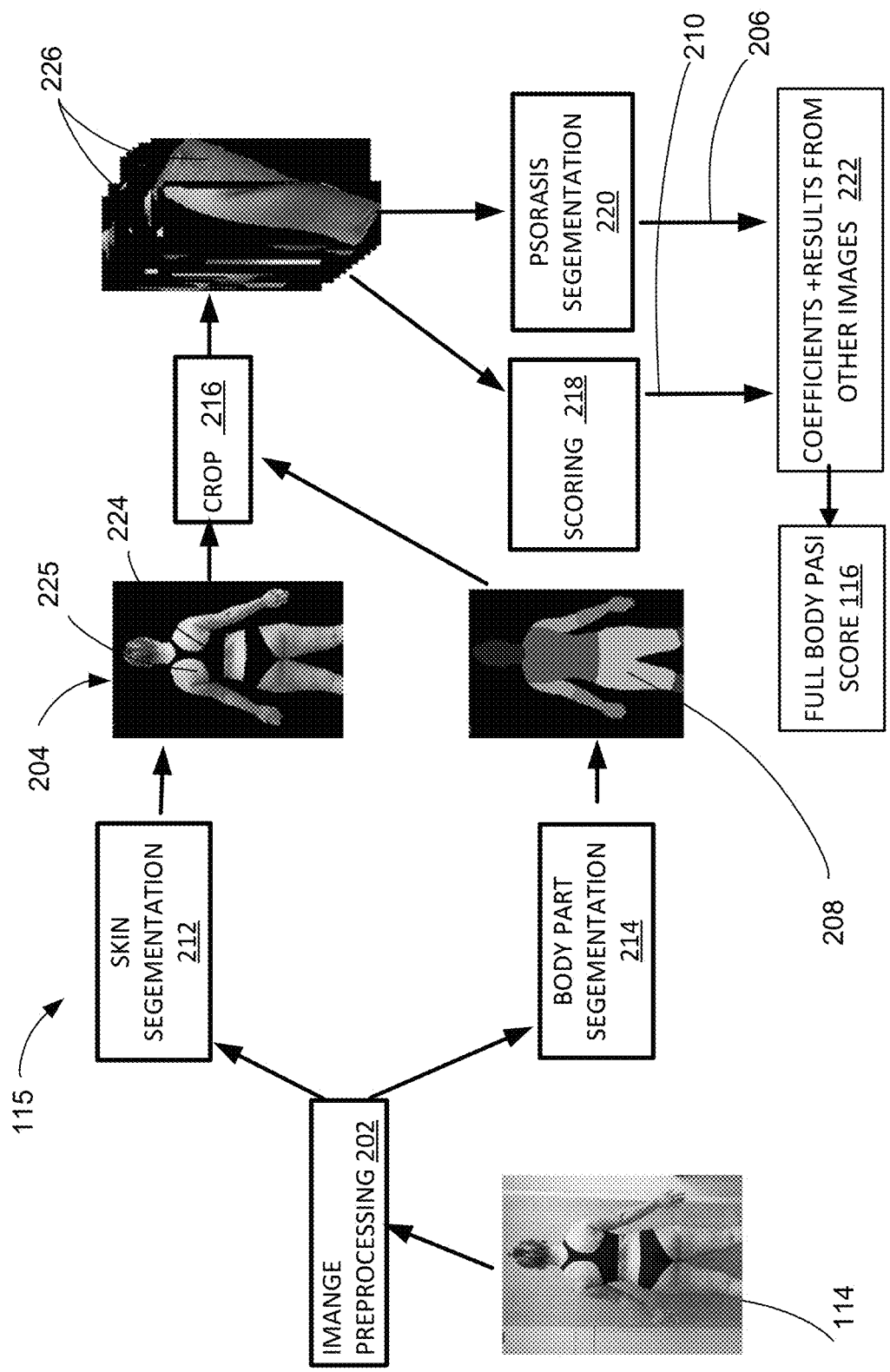
FIG. 2 is an example of a control flow of the compute system with the psoriasis diagnostic mechanism in an embodiment.

Referring now to FIG. 2, therein is shown an example of a control flow of the compute system 100 of FIG. 1 with the psoriasis diagnostic mechanism in an embodiment. As a specific example, FIG. 2 can depict a flow of the psoriasis diagnostic module 115. The psoriasis diagnostic module 115 computes the full body PASI score 116 as well as local psoriasis scores based on the patient images 114 uploaded for a patient.

The compute system 100 process the patient images 114, each of which can covers a specific part of the body (e.g. the back, the shin, etc.), multiple body parts, different angles of one or more of the body parts, or a combination thereof so that the patient images 114 cover the full body of a patient or portions of the full body of the patient to be analyzed. As a specific example, the compute system 100 can process as few as four (4) and more than twenty (20) images that cover the full body. In this example, the patient images 114 cover body parts including arms, back; arms, front; arms, left; arms, right; back; back of head; back of thigh; calves; forearms, bottom; forearms, top; front face; front of thigh; front trunk; left calf; left face; left flank; left thigh; palms; right calf; right face; right flank; right thigh; shins; soles; top of feet; top of hands; and top of head. The compute system 100, the psoriasis diagnostic module 115, or a combination thereof can compute the full body PASI score 116 if there are twenty seven (27) images for the patient. In this example, if there are missing images, all scores related to those images are assigned as zero.

The compute system 100, the psoriasis diagnostic module 115, or a combination thereof can provide the full body PASI score 116 for the patient based in the patient images 114 loaded for that patient and for that set of the patient images 114. In this example for each of the body parts (example shown in Table 1) of the patients (head and neck; trunk; upper extremities; lower extremities), there are 4 scores in the output, that are used in the computation of the full body PASI score 116.

TABLE 1

| Body Region | Redness | Thickness | Scaling | Percent Involvement | Multiplier | Score per Body Region |
|---|---|---|---|---|---|---|
| Head/Neck | 1.11 | 0.73 | 1.22 | 16.71% | 0.1 | 0.5037 |
| Trunk | 2.14 | 1.52 | 1.75 | 33.7% | 0.3 | 4.2028 |

TABLE 1-continued

| Body Region | Redness | Thickness | Scaling | Percent Involvement | Multiplier | Score per Body Region |
|---|---|---|---|---|---|---|
| Upper Extremities | 1.32 | 1.88 | 2.32 | 51.75% | 0.2 | 3.9772 |
| Lower Extremities | 1.6 | 1.99 | 2.48 | 62.21% | 0.4 | 10.1652 |
| | | | Full Body PASI Score sum for 4 body region score | | | 18.8489 |

The "Percent Involvement" in Table 1 represents the surface area of the skin affected by psoriasis and represents a ratio over the surface area of the body part. The "Redness" in Table 1 represents erythema severity score of the affected skin. The "Thickness" in Table 1 represents the induration severity score of the affected skin. The "Scaling" in Table 1 represents severity score of the affected skin.

In this example for an embodiment, the psoriasis diagnostic module 115 can preprocess the patient images 114 to determine if each of the patient images 114 should proceed to be utilized to compute the full body PASI score 116. As an example, an image preprocessing module 202 can determine if the psoriasis diagnostic module 115 each of the patient images 114 to be accepted or rejected for computing the full body PASI score 116. The image preprocessing module 202 can determine whether or not each of the patient images 114 include skin area to be utilized for computing the full body PASI score 116. If the instance of the patient images 114 does include the skin area to be utilized, then that particular instance of the patient images 114 is eligible to continue to be processed. The image preprocessing module 202 can determine if each of the patient images 114 meet or exceed quality measures to be continue to be processed, otherwise the instance of the patient images 114 not meeting the quality measures are rejected.

The compute system 100, the psoriasis diagnostic module 115, or a combination thereof can provide intermediate output for each of the patient images 114, allowed to continue processing by the image preprocessing module 202. The intermediate output for each of the patient images 114 can include a skin segmentation 204, a psoriasis segmentation 206, a body part segmentation 208 of detailed body parts (e.g., "upper extremities" are divided into "upper arm", "lower arm", "hand"), a division of each of the patient images 114 into several smaller pieces, and intermediate scores 210 (erythema, induration, desquamation) for each of the detailed body parts from the body part segmentation 208.

In this example, the compute system 100, the psoriasis diagnostic module 115, or a combination thereof can compute the final output or the full body PASI score 116 from the intermediate scores 210.

As an example, the control flow shown in FIG. 2 includes the image preprocessing module 202, a skin segmentation model 212, a body part segmentation model 214, a crop module 216, a scoring model 218, a psoriasis segmentation model 220, and an aggregation module 222. A set of the patient images 114 for each patient are inputs to the image preprocessing module 202. The patient images 114 that passes the preprocessing by the image preprocessing module 202 proceed to the skin segmentation model 212 and the body part segmentation model 214. The aggregation module 222 outputs the full body PASI score 116.

The skin segmentation model 212 generates a skin prediction 225 from an image being processed. As an example, the skin prediction 225 can be shown with blackout non-skin regions 224 from each of the patient images 114. The non-skin regions 224 are the region in the each of the patient images 114 covered by clothing or other obstruction over the body or body part covering up the skin. The skin segmentation model 212 also takes into the account of the skin color or hue of the patient to distinguish between skin of the patient and non-skin portion of the patient.

The body part segmentation model 214 fits each of the patient images 114 into 8 different body parts. The 4 body regions in Table 1 are mapped to the 8 body parts as follows. In this specific example, there are over 20 instances of the patient images 114 for each of the patient and those determined by the image preprocessing module 202 for continued processing. The patient images 114 include those for each patient's arms, back; arms, front; arms, left; arms, right; back; back of head; back of thigh; calves; forearms, bottom; forearms, top; front face; front of thigh; front trunk; left calf; left face; left flank; left thigh; palms; right calf; right face; right flank; right thigh; shins; soles; top of feet; top of hands; and top of head.

The body region for Head/Neck include the patient images 114 with associated head and neck (5 images in total). The body region for Trunk include the patient images 114 associated with the trunk of a patient (5 images in total). The body region for the Upper Extremities include the patient images 114 for the Upper Limbs (elbow upwards and elbow downwards, 6 images in total), and Hands and Palms (2 images in total). The body region for the Lower Extremities include the patient images 114 associated with the Lower Limbs (shin and thighs, 6 images in total), and Fee and Soles (2 images in total).

The flow progresses to the crop module 216. In this example, the crop module 216 inputs the outputs from the skin segmentation model 212 and the body part segmentation model 214 to crop or isolate portions of the patient images 114 with the non-skin regions 224. Continuing with the specific example of 27 patient images 114, the crop module 216 can generate up to 69 cropped images 226. In this example, the cropped images 226 include those for arms, back—['upper limbs (elbow upwards)', 'upper limbs (elbow downwards)', 'trunk']; arms, front—['upper limbs (elbow upwards)', 'upper limbs (elbow downwards)', 'trunk']; arms, left—['upper limbs (elbow upwards)', 'upper limbs (elbow downwards)']; arms, right—['upper limbs (elbow upwards)', 'upper limbs (elbow downwards)']; back—trunk; back of head—head and neck; back of thigh—lower limbs(thigh); calves—lower limbs (shin); forearms, bottom—upper limbs (elbow downwards); forearms, top—upper limbs (elbow downwards); front face-head and neck; front trunk—trunk; front of thigh—lower limbs (thigh); left calf—lower limbs (shin); left face—head and neck; left flank—trunk; left thigh—lower limbs(thigh); palms-hands and palms; right calf—lower limbs (shin); right face—head and neck; right flank—trunk; right thigh—lower limbs (thigh); shins—lower limbs (shin); soles—feet and soles; top of feet-feet and soles; top of hands—hands and palms; top of head—head and neck.

For each of the patient images 114 and body part, the crop module 216 will crop the patient images 114 based on body part output from the body part segmentation model 214, then will blackout the non-skin regions 224 based on the skin prediction 225 to generate the cropped images 226. As a specific example, the skin segmentation model 212 can generate a zero value as part of the skin prediction 225 for the pixels for the non-skin regions 224 of the patient images 114 and the crop module 216 black out non-skin regions 224 based on each of the pixel with the zero value. In this example, each of the cropped images 226 corresponds to a specific body part.

In this example, the total number of cropped images 226 is greater than the number of patient images 114, and the cropped images 226 together cover the full body. In the specific example with 27 patient images 114, the number of the cropped images 226 is 69. The patient images 114 may be overlapping (so each point on the body may be covered either once, or 2-3 times, and the protocol allows us to know which part of the body is covered how many times by the patient images 114).

The flow can progress to the scoring model 218, the psoriasis segmentation model 220, or a combination thereof. The psoriasis segmentation model 220 processes the each of the cropped images 226. The scoring model 218 processes each of the cropped images 226. The psoriasis segmentation model 220 computes a psoriasis area or the psoriasis segmentation 206, one or more, for each of the cropped images 226 based on the non-skin regions 224 and the skin prediction 225. The scoring model 218 computes the values for the intermediate scores 210 for redness, thickness, and scaliness for each of the cropped images 226 based on the non-skin regions 224 and the skin prediction 225.

The flow can progress to the aggregation module 222. The aggregation module 222 computes the PASI score for each of the body part based on the results from the scoring model 218, the psoriasis segmentation model 220, or a combination thereof. Table 1 depicts an example of an output of the aggregation module 222. In the specific example, the aggregation module 222 receives results for the 69 cropped images 226 from the scoring model 218, the psoriasis segmentation model 220, or a combination thereof.

As an example, the aggregation module 222 process the results from the cropped images 226 for each of the body region (as shown in Table 1), head and neck, trunk, upper extremities (including upper limbs, and hands and palms), lower extremities (including lower limbs, and feet and soles).

In this example, the aggregation module 222 computes score of each body region based on Equation 1 below, where $S_{bodypart}$ be the score of a given body part, S can be E (erythema or redness), I (Induration or thickness) or S (Scaliness).

$$S_{bodypart} = \frac{\sum S_i C_i A_i / B_i}{\sum C_i A_i / B_i} \qquad \text{Equation 1}$$

Continuing with this example, the aggregation module 222 computes the affected area, $R_{bodypart}$, of the region based on Equation 2 below.

$$R_{bodypart} = \frac{\sum C_i A_i / B_i}{\sum C_i} \qquad \text{Equation 2}$$

Further continuing with this example, the aggregation module 222 computes the PASI score of a body region (rightmost column in Table 1), $PASI_{bodypart}$, based on Equation 3 below.

$$PASI_{bodypart} = f(R) \times (E + I + S) \qquad \text{Equation 3}$$

Where:
$S_i$: Score of image i in the list of concerned images (in this example, the cropped images 226). To compute redness, S is redness score. To compute thickness, S is thickness score, etc. An example of these scores are populated in the columns in Table 1.
E, I, S is redness, thickness and scaliness score of each body region. An example of these scores are populated in the columns in Table 1.
$C_i$: Coefficient of image i in the list of concerned images (in this example, the cropped images 226). This coefficient can be found in the "Name convention" table in the shared document. An example of these scores are populated in the columns in Table 1.
$A_i$: Affected area of cropped image i in the list of concerned images (in this example, the cropped images 226). It is the area of segmented psoriasis on that cropped image.
$B_i$: Body part area of the cropped image i in the list of concerned images (in this example, the cropped images 226). It is the area of segmented body part.
$f(R)$ is conversion function. This function convert from percentage of involvement into score (from 0 to 6). R represents the percent involvement in Table 1. An example of the conversion function is expressed in Equation 4.

The aggregation module 222 utilizes the results from Equation 1, Equation 2, and Equation 3 to compute $S_{bodypart}$ (redness, thickness and scaliness), affected area $R_{bodypart}$ and $PASI_{bodypart}$ for each body part or the body part segmentation 208: head/neck, trunk, lower extremities, upper extremities. From these information, the compute system 100 can compute full body PASI score 116 for this set of the patient images 114 (27 images in this example) by taking the sum of $PASI_{bodypart}$ of all body parts, as shown as an example PASI scoring table in Table 1.

Figure 3:
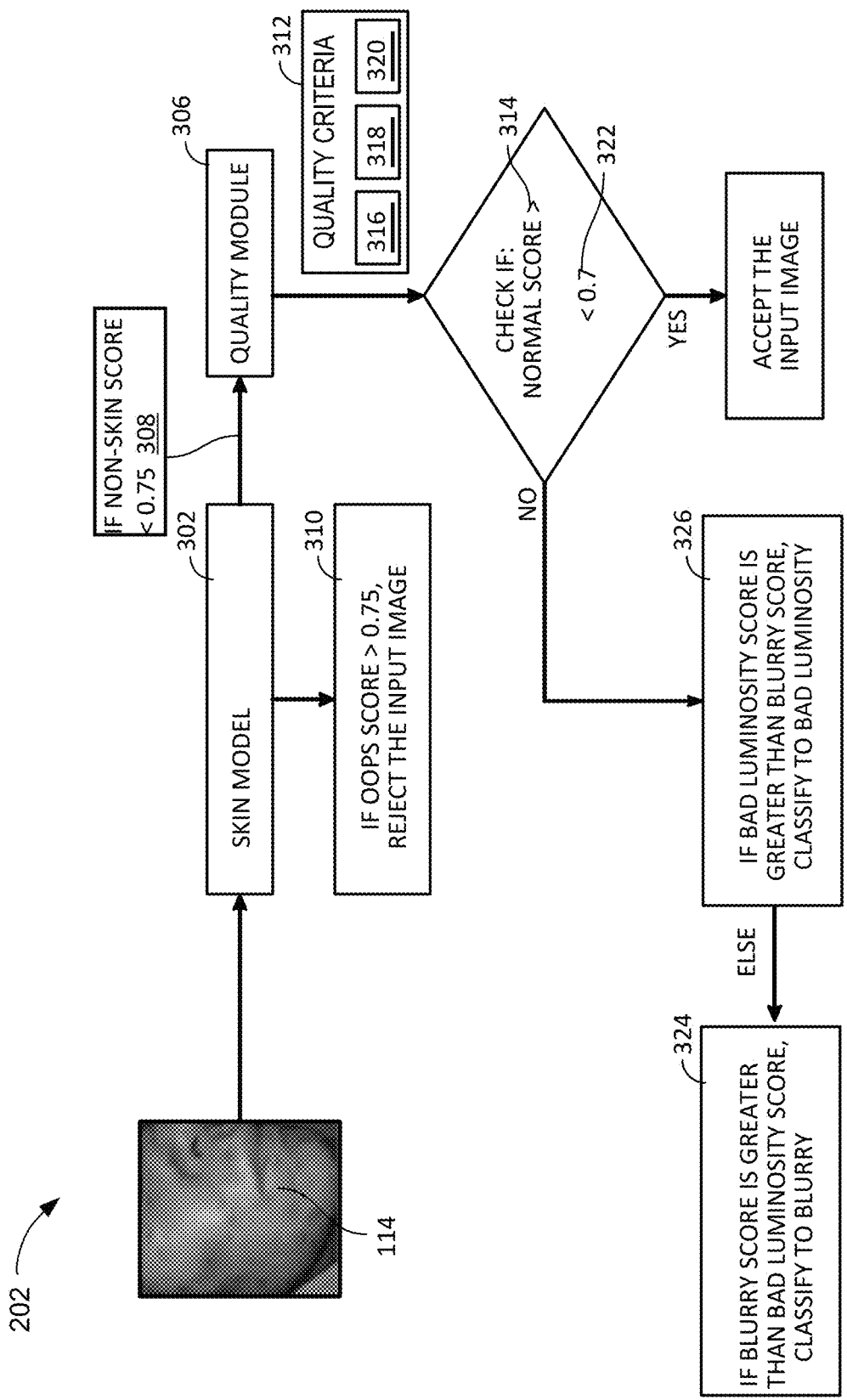
FIG. 3 is an example of an image preprocessing module in an embodiment.

Referring now to FIG. 3, therein is shown an example of the image preprocessing module 202 in an embodiment. The image preprocessing module 202 determines which of the patient images 114 meets criteria to continue to be processes by the psoriasis diagnostic module 115 of FIG. 2 and which should be rejected and not continued to be processed to be used to calculate the full body PASI score 116 of FIG. 2. In this example, the image preprocessing module 202 can include an skin module 302, the quality module 306, or a combination thereof.

The skin module 302 can check if each instance of the patient images 114 being input to the psoriasis diagnostic module 115 includes skin regions large enough to check for skin conditions. The skin module 302 can be implemented in a number of ways.

For example, the skin module 302 can be implemented with a machine learning model or neural network model. As a specific example, the skin module 302 can set a threshold for a non-skin score 308 to determine the instance of the patient images 114 being processed includes skin regions to be usable to determine if a skin condition exists or not. As a further specific example, a non-nominal threshold 310 can be set at 0.75. If the skin module 302 determines the non-skin score 308 to be equal to or greater than non-nominal threshold 310, then the instance of the patient images 114 being process is rejected. If the non-skin score 308 is less than or equal to the non-nominal threshold 310, then the instance of the patient images 114 being process is accepted and the process can proceed to the skin detection module 304.

As an example, the non-nominal threshold 310 can represent a number of skin related aspects of the content in each of the patient images 114. For example, the non-nominal threshold 310 can represent a comparison on whether or not the image being analyzed as a candidate as one of the patient images 114 is even relevant to the skin or to even a human being. As a specific example, the patient images 114 can be for cars, flowers, trees, animals, clothes, etc. and are rejected for being meeting or exceeding the non-nominal threshold 310 because there is no skin or human skin in the rejected as in the examples noted.

As another example, the non-nominal threshold 310 can represent a portion for each of the patient images 114 being analyzed as categorizing the amount of human and non-human content. As a specific example, the image analyzed as one of the patient images 114 can include a hand holding a large flower where the flower and background is over 80% of the area of the image and the hand is only visible less than 20% such that the non-human content would be meeting or exceeding the non-nominal threshold 310.

As a further example, the non-nominal threshold 310 can represent the amount of human skin visible in the image analyzed as one of the patient images 114 even though that particular image is a group of people in a group photo but all wearing heavy cold weather coats covering most of their body and skin. In this example, this example of the image would be rejected for being meeting or exceeding the non-nominal threshold 310.

As a different example, a picture of a person or a group of people in summer swim wear exposing more than half of the body skin might be below the non-nominal threshold 310 if there is enough details of the skin to make a diagnosis of a skin ailment regardless the amount of skin area relative to the entire area of the image.

The rejection of the image can be used for training the skin module 302 of what type of images are to be rejected and what value to generate for the non-skin score 308. The acceptance of the image can be used for training the skin module 302 of what type of images are to be accepted and what value to generate for the non-skin score 308. The training process for the skin module 302 can also be used to determine the value of the non-nominal threshold 310 to accept or reject. In the example shown in FIG. 3, the patient images 114 accepted by the skin module 302 can continued to be processed.

The quality module 306 can check the patient images 114 from the skin module 302, the skin detection module 304, or a combination thereof for progressing in processing through the psoriasis diagnostic module 115. The quality module 306 can be implemented in a number of ways.

For example, the quality module 306 can check the patient images 114 that are input for certain quality criteria 312 and meeting or exceeding a quality threshold 314. As specific examples, the quality criteria 312 can include a nominal metric 316, a blurry metric 318, a bad luminosity metric 320, or a combination thereof. Further as a specific example, the quality criteria 312 is a three dimensional vector with the nominal metric 316, the blurry metric 318, and the bad luminosity metric 320.

The nominal metric 316 is used to measure the acceptability of the patient images 114 beyond the acceptability by the skin module 302. The skin module 302 rejects or accepts each of the patient images 114 to include sufficient skin area or skin region as described earlier. The nominal metric 316 processes the patent images 114 further such that the image is of sufficient quality to determine a skin diagnosis. The nominal metric 316 represents an overall measure that can be used to determine the acceptability of the image for skin diagnosis for further processing. The nominal metric 316 can include indications for clarity, lighting, non-intervening obstructions to the visibility of skin, resolution, or a combination thereof.

The blurry metric 318 is used to measure the how clear or blurry the image being processed is. The value for blurry metric 318 is set for an image used for training the quality module 304 of what is considered clear and what is consider not clear or blurry. If the value of the blurry metric 318 indicates that the image is not clear or blurry, then the psoriasis diagnostic module 115 or portions thereof cannot analyze the instance of the patient images 114 to compute the full body PASI score 116 of FIG. 2. If the value of the blurry metric 318 indicates that the image is clear or not blurry, then the psoriasis diagnostic module 115 or portions thereof can analyze the instance of the patient images 114 to compute the full body PASI score 116.

The bad luminosity metric 320 is used to measure the lighting or brightness or dimness the image being processed is. The value for bad luminosity metric 320 is set for an image used for training the quality module 304 of what is considered too dim and what is consider not dim. If the value of the bad luminosity metric 320 indicates that the image is dim, then the psoriasis diagnostic module 115 or portions thereof cannot analyze the instance of the patient images 114 to compute the full body PASI score 116 of FIG. 2. If the value of the bad luminosity metric 320 indicates that the image is not too dim, then the psoriasis diagnostic module 115 or portions thereof can analyze the instance of the patient images 114 to compute the full body PASI score 116.

The metrics of the quality criteria 312 can measured with quality threshold 314 collectively, as subsets, as equal priority, or of non-equal priority. The term equal priority refers to all the metrics are compared with equal weight and impact the meeting or exceeding the quality threshold 314 for the image to be deemed acceptable and continue to be processed by the psoriasis diagnostic module 115. The term non-equal priority refers to the varying weight of the metrics relative to each other where some can have more importance over the other metrics. As an example, one of the metrics of the quality criteria 312 alone can be used to determine if the quality threshold 314 is met or not for the image to continue to be processed by the psoriasis diagnostic module 115.

Returning to the quality threshold 314, the quality threshold 314 can include a single value for all or some of the metrics of the quality criteria 312 or can include a value for each of the metrics of the quality criteria 312. As an example, the quality threshold 314 can include a nominal threshold 322, a blurry threshold 324, a bad luminosity threshold 326, or a combination thereof.

As a specific example, if an instance of the patient images 114 is relevant or usable to compute the full body PASI score 116 by the psoriasis diagnostic module 115, then the skin module 302 determined that instance of the patient images 114 continues processing to the quality module 306. In this example, the quality module 306 checks each of the instance of the patient images 114 and outputs a three dimensional vector for the scores for the nominal metric 316, the blurry metric 318, and the bad luminosity metric 320. The value for the bad luminosity metric 320 can also represent the noise in the image being processed.

Continuing with the specific example, the sum of output vector for the quality criteria 312 does not need to be 1. There can be two high values at the same time: [0.0, 99.6, 98.0] for the nominal metric 316, the blurry metric 318, and the bad luminosity 320, respectively, which means the input image can be blurry or not clear and in bad light quality.

The compute system 100 can set a nominal threshold 322 for the nominal metric 316 for example, if the value for the nominal metric 316 is greater than or equal to 0.6, the quality module 306, the psoriasis diagnostic module 115, or a combination thereof accept the input image or the instance of the patient images 114 being processed at the time. In other words, the nominal metric 316 greater than or equal to the nominal threshold 322 alone can be the quality criteria 312 and serve as the quality threshold 314, respectively, to determine the patient images 114 being processes as acceptable by the quality module 306. In this example, the quality criteria 312 can function as a priority encoder with the nominal metric 316 greater than or equal to the nominal threshold 322 to determine acceptability regardless of the values and comparison to the other two metrics and two thresholds.

When the nominal metric 316 is less than the nominal threshold 322, the blurry metric 318 and the bad luminosity metric 320 are compared to the blurry threshold 324 and the bad luminosity threshold 326, respectively. The greater or the maximum value between the blurry metric 318 and the bad luminosity metric 320 will determine whether the blurry threshold 324 or the bad luminosity threshold 326, respectively, shall be used as the quality threshold 314.

In other words, as an example, if the value of the nominal metric 316 is lower than 0.6 but values for the blurry metric 318 and the bad luminosity metric 320 indicates bad light condition are lower than the blurry threshold 324 and the bad luminosity threshold 326, respectively, then the quality module 306, the psoriasis diagnostic module 115, or a combination thereof accept the input image or the instance of the patient images 114 being processed at the time. Otherwise, the input image or the instance of the patient images 114 being processed at the time will be classified into blurry if the value for the blurry metric 318 is higher than the value for the bad luminosity metric 320 and vice versa. Continuing this example, the quality threshold 314 is shown to be 0.7. Further, the metric (blurry metric 318 or the bad luminosity metric 320) with the larger value can be used to provide feedback to improve performance of the compute system 100 if the quality module 306 rejects the image.

Figures 4, 5:
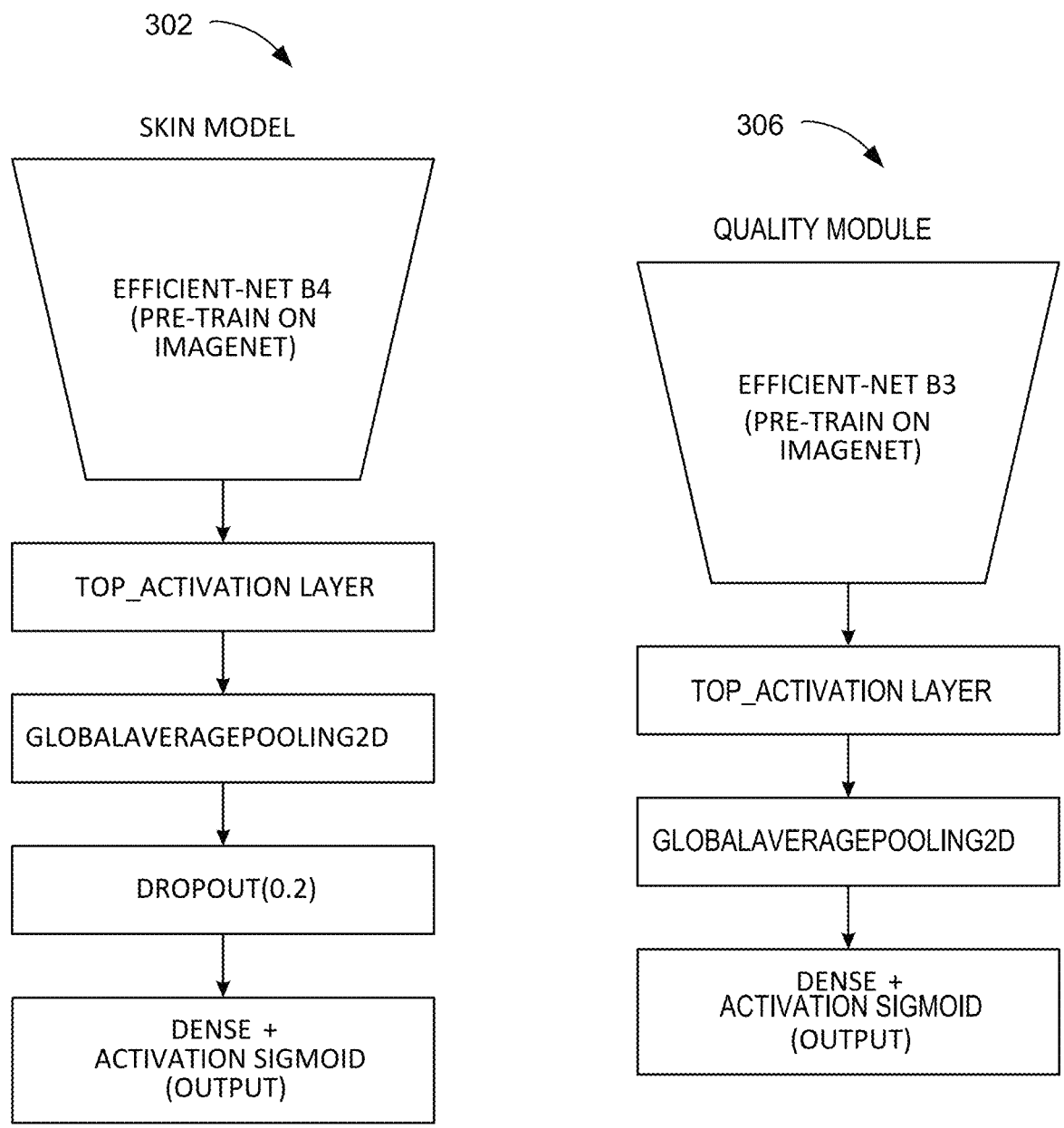
FIG. 4 is an example of a skin module in an embodiment.
FIG. 5 is an example of a quality module in an embodiment.

Referring now to FIG. 4, therein is shown an example of the skin module 302 in an embodiment. The skin module 302 can be implemented in a number of ways. For example, the skin module 302 can be implement with various machine learning or neural network mechanisms. For example, the skin module 302 utilizes transfer learning. Transfer learning is a technique used in machine learning to improve learning performance of new task by using knowledge from another different but related task.

As a specific example shown in FIG. 4, the skin module 302 can be implemented with an Efficient-net B4 pre-trained on ImageNet until the last layer. In other words, the skin module 302 can be implemented utilizing transfer learning from a pre-trained Efficient-net B4 on ImageNet dataset. Pre-trained Efficient-net was implemented utilizing library tensor flow. The output of pre-trained Efficient-Net B4 on ImageNet contains 1000 components whereas output of the skin module 302 includes 1 component, so the skin module 302 is implemented with modification to the top last layers so that the new architecture is adapted with the output structure of the skin module 302. As a specific example, the ImageNet includes a large dataset which contains about 1.28 million images with 1000 object classes. After the pre-training process, the Efficient-net B4 model can extract features from images. Then the skin module 302 is trained with our dataset for psoriasis, the skin module 302 is honed into our targets for psoriasis.

When output is the same, the same architecture can be utilized for the implementation, such as keep the same backbone Efficient-net B4. Otherwise as for the implementation of the skin module 302, the output is different and the implementation includes modification to the top layers so that the new architecture still keeps much of the architecture of Efficient-net (by keeping until top activation layer) and its output is adapted for the skin module 302 (by adding new Pooling, Dropout and Dense layers).

After loading the pre-trained weights, the last layer (top-activation layer) contains the key features of the image. The skin module 302 is implemented with a reduction of the size of the layer by using average pooling technique to take the average values of the features layer. With the skin module 302, the implementation in this example utilizes dropout to avoid over-fitting, such that the skin module 302 will not learn-by-heart the classes of the input images but really learn the features and classify correctly. The skin module 302 is also implemented with the dense+ activation to get the output vector.

As a specific example, the skin module 302 performs global pooling+ Dropout before a Dense layer to get the output. The Skin module 302 can be implemented to support the artificial intelligence of the psoriasis diagnostic module 115 related to skin condition prediction. In other words, the skin module 302 determines an image being process is a relevant image or acceptable image as an image including skin. The skin part should be close enough such that a doctor can see if there is any skin condition.

As examples, the skin module 302 should reject images that includes skin but the skin regions are not large enough in the image for a doctor to seek if there is any skin condition, such as a picture of a circus trapeze act, hands or partial arms reaching over a dining table, a partial hand holding a donut, a person's head while taking a bite of a pizza slice, a partial hand holding a burger. While these images include some skin, the images do not include enough or angles of the skin or size the skin for a doctor to see if there is any skin condition and the skin module 302 would be trained to reject these types of images. Also as a specific example, the skin module 302 outputs a score from 0 to 1 for each input image. After the testing phase with thousands of images, the skin module 302 considers an image to be rejected for skin condition analysis for a threshold above or greater than 0.75.

Referring now to FIG. 5, therein is shown an example of the quality module 306 in an embodiment. The quality module 306 implemented in a number of ways. For example, the quality module 306 can be implement with various machine learning or neural network mechanisms. The quality module 306 can be implemented utilizing transfer learning similarly described in FIG. 4.

As a specific example shown in FIG. 5, the quality module 306 can be implemented with an Efficient-net B3 pre-trained on ImageNet until the last layer. The quality module 306 performs global pooling before a Dense layer to get the output. The quality module 306 can be implemented to support the artificial intelligence of the psoriasis diagnostic module 115.

The quality module 306 will classify an input image into three different categories (1) acceptable image: image has good quality for skin condition prediction, (2) blurry image, (3) bad luminosity image: image taken under bad light condition such as too dark, too light or too noisy. The first category "(1)" is represented by the nominal metric 316 of FIG. 3. The second category "(2)" is represented by the blurry metric 318 of FIG. 3. The third category "(3)" is represented by the bad luminosity metric 320 of FIG. 3.

As described in FIG. 3 as an example, the quality module 306 can output a vector of three dimensions for each input image. The output vector is the value for [the nominal metric 316, the blurry metric 318, the bad luminosity metric 320]. The value for each of the metric is from 0 to 1. The bigger score is, the closer to the category. For the nominal metric 316, the higher value indicates the image is closer to being acceptable to skin condition prediction. For the blurry metric 318, the higher the value indicates the image is more blurry and not clear. For the bad luminosity metric 320, the higher the value indicates the image is taken or reflect bad lighting, such as being dim or shadowing from the angle of lighting. After the training and testing phase through thousands of images), the threshold for each category is determined. Basically it is a manual process.

As in the example shown in FIG. 3, if the value for the nominal metric 316 is greater than 0.6, the quality module 306 determines to accept the input image. If the value for the nominal metric 316 is lower than 0.6 but the score for blurry and bad light condition are lower than or equal their threshold 0.7, then quality module 306 determines the input image is acceptable. In other words, both the value for the blurry metric 318 and the value of the bad luminosity metric 320 is less than or equal to the blurry threshold 324 and the bad luminosity threshold 326, respectively. Otherwise, the quality module 306 will determine or classify the input image as blurry or not clear if the value for the blurry metric 318 is higher than bad luminosity metric 320 and vice versa. As shown in the example in FIG. 3, the Max(output) refers to the maximum value of the output vector that is the maximum value of each score for acceptable, blurry, bad light condition. For example: output vector is [0.0, 100.0, 98.4], the Max(output)=100.0, Referring now to FIG. 6, there in shown an example of a graphical representation of the function of a conversion function of the compute system 100 of FIG. 1 with the psoriasis diagnostic mechanism in an embodiment. The conversion function, $f(R)$, utilized in Equation 3 can be implemented by Equation 4, as an example, below of the conversion of the percentage involvement into a score, an example is shown in Table 2 below.

$$f(R)=20\times\min(R,0.05)+(^5\%)\times\min(0.9,\max(R-0.05,0)) \quad \text{Equation 4}$$

The conversion function expressed in Equation 4 improves on the translation from Table 2 below to area of involvement, where each body area has potentially 100% involvement. Score 0-6 based on the Table 2. Examples of the improvements with the use of the conversion function, $f(R)$, expressed in Equation 4 over the use of Table 2 can be seen in FIG. 6.

TABLE 2

| | Area of Involvement to score from 0 to 6 | | | | | | |
|---|---|---|---|---|---|---|---|
| Percent Involvement | 0 | 1-9 | 10-29 | 30-49 | 50-69 | 70-89 | 90-100 |
| Region Score | 0 | 1 | 2 | 3 | 4 | 5 | 6 |

Figure 6:
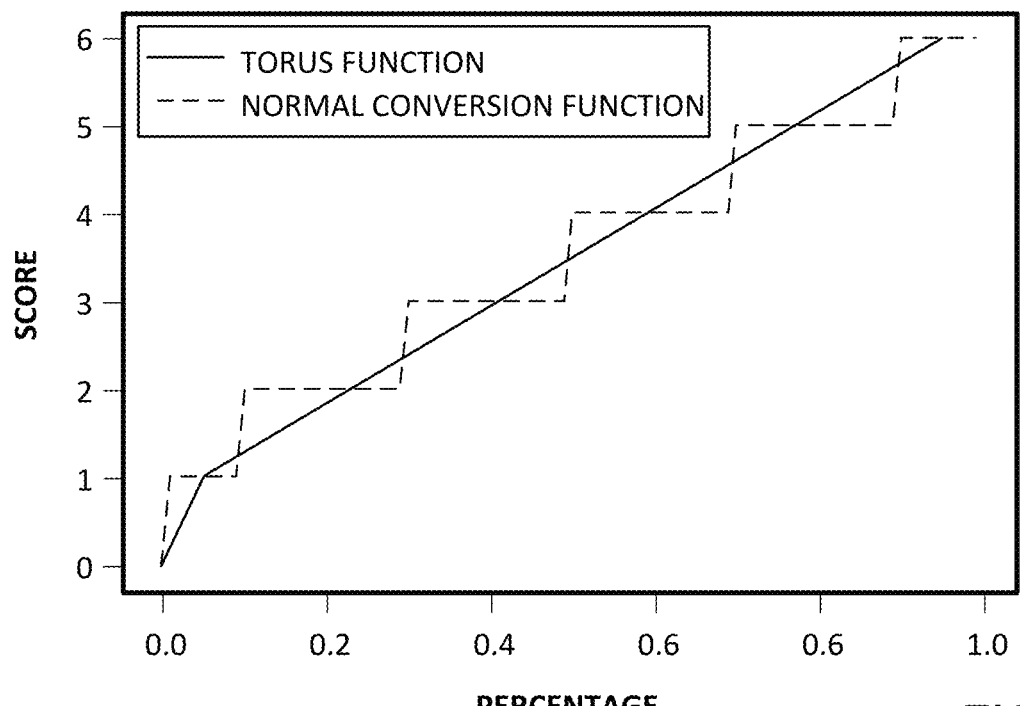
FIG. 6 is an example of a graphical representation of the function of a conversion function of the compute system with the psoriasis diagnostic mechanism in an embodiment.

In this example, the conversion function translates the affected area to an area score that is a continuous function, as an example shown in FIG. 6 as a non-step wise function or nearly linear plot. The x-axis is shown as Percent Involvement and the y-axis is the Region Score. In other words, the conversion function smooths out the PASI system.

In the example depicted in FIG. 6, in the original system 20%-50% equals surface area score 3, 50%-80% equals score 4. A small change in BSA from 49:9% to 50% can lead to a big jump in the score. The conversion function formula makes the translation from affected area to area score becomes a continuous function leading to a more precise and accurate score and diagnostic aide. In particular, 50% equals surface area score 3.5 (not 3, not 4, but 3.5).

Figure 7:
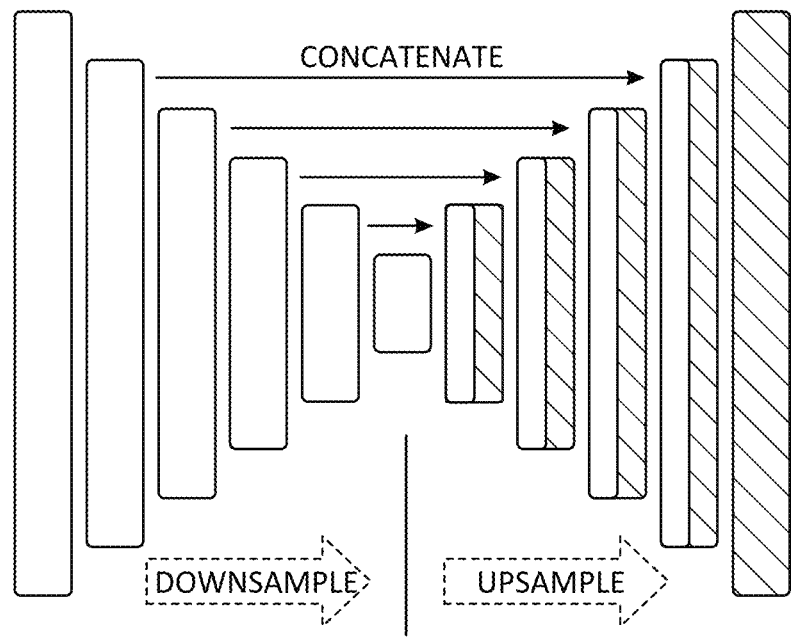
FIG. 7 is an example of a block diagram of models of the psoriasis diagnostic mechanism of the compute system.

Referring now to FIG. 7, therein is shown an example of a block diagram of models of the psoriasis diagnostic mechanism of the compute system 100 of FIG. 1. The example depicted in FIG. 7 can represent a U-net architecture utilized in one form or another for the skin segmentation model 212 of FIG. 2, the body part segmentation model 214 of FIG. 2, the psoriasis segmentation model 220 of FIG. 2, or a combination thereof.

Regarding the skin segmentation model 212, this model segments all skin region including eyes, nails, sick skin (for example skin with psoriasis, skin with skin cancer, etc.) in the input image or in our embodiments the patient images 114 of FIG. 2. The skin segmentation model 212 also segment skin under hair and ignores the object on or over the skin such as glasses, clothes, bracelet, etc. However, the skin segmentation model 212 still segments the visible skin even if the portion of the skin has something over it, such as the skin under glasses or hair that can be transparent, translucent, or partially cover the portion of the skin which can be a suspect area for psoriasis.

The skin segmentation model 212 is trained with data sets that include variety in resolution images (both very closed up shot to wide shot). The data sets also includes images with very sick skin to normal skin in wide range of skin tone from white to darker skin. As an example, the training data set was annotated with a graphic editor to annotate skin and non-skin regions, even if the skin region is under a covering over the skin but still visible or at least partially visible. After annotation work, all the data set was double-checked by a test team to make sure that there was no error in the training set.

In an example, the skin data set includes 1402 images with smallest size of 192×127 pixels and maximum size of 4096×5462 pixels. The compute system 100 also performed input synthesis to enrich the training data set by resizing or random cropping each image to a size of 384×384 pixels and many other technique in augmentation of the data set during training, such as adding noise, adding brightness, rotating, flipping, shifting, or a combination thereof.

As noted earlier, the skin segmentation model 212 utilizes a U-net architecture. The U-net architecture is a convolutional neural network for segmentation of images. The U-net architecture provides an end-to-end approach taking in images to be analyzed and output segmented information for the images being analyzed.

As a specific example, the skin segmentation model 212 utilizes a U-net architecture, which includes a specific encoder-decoder scheme. The encoder reduces the spatial dimensions in every layer and increases the channels. On the other hand, the decoder increases the spatial dimensions while reducing the channels. As a specific example, the skin segmentation model 212 can be implemented with the U-net architecture found in Ronneberger, Olaf; Fischer, Philipp; Brox, Thomas (2015). "U-Net: Convolutional Networks for Biomedical Image Segmentation", which is herein incorporated by reference in its entirety.

The skin segmentation model 212 provides a scaling method to the U-net convolution neural network. The skin segmentation model 212 utilizes pre-trained model and utilizes transfer learning. The skin segmentation model 212 performs scaling by uniformly scales all dimensions of depth, width, and resolution using a compound coefficient. As an example, the skin segmentation model 212 includes 508 layers with 25.7 million parameters. As a specific example, the skin segmentation model 212 can be implemented with EfficientNet, an architecture for classification problem which is pre-trained on ImageNet data set, for the encoding part. Also as a specific example, the skin segmentation model 212 can be implemented with Markoff, John (19 Nov. 2012). "For Web Images, Creating New Technology to Seek and Find" The New York Times. Retrieved 3 Feb. 2018, which is herein incorporated by reference in its entirety.

The loss function plays an importance role in the training process. The loss function of the skin segmentation model 212 punish the model if it segments off lesion region as well as not does not segment skin area. An example of the loss function can be expressed in the pseudo code below:

$$l(y,\hat{y})=1-\Sigma_{i,j}f_1/\Sigma_{i,j}f_2 \quad \text{Equation 5}$$

Where $f_1=1-(1-y_1)^k$, $f_2=1-(1-y_2)^h$, $y_1=y\hat{y}$, $y_2=(1-y)(1-y)$, h=2.5, k=2.5, $\hat{y}$ is the true label and $\hat{y}$ is the prediction. The sum in the Equation 5 of the loss function l is taken over two indices: index i stands for the index of data sample $\{y_i\}_i$, index j stands for the component of the vector label $y_i=(y_{ij})_j$. This loss consider not only the mask (y and $\hat{y}$) but also in the inverse mask (1−y and 1−1−$\hat{y}$). By varying parameters h,k the modules that utilizes this loss function in the psoriasis diagnostic module 115 can have different version of this loss function for different purposes. For example, if the psoriasis diagnostic module 115 has a value with a lower k and increased value for h, the modules will increase the priority area of the pixels valued 1 (e.g. for the skin area or skin region) compared to the area of pixels valued 0 (e.g. for non-skin area or non-skin region). As an example, h=k=2.5 allows the modules to balance priority for the skin area compared to the non-skin area.

Figure 8:
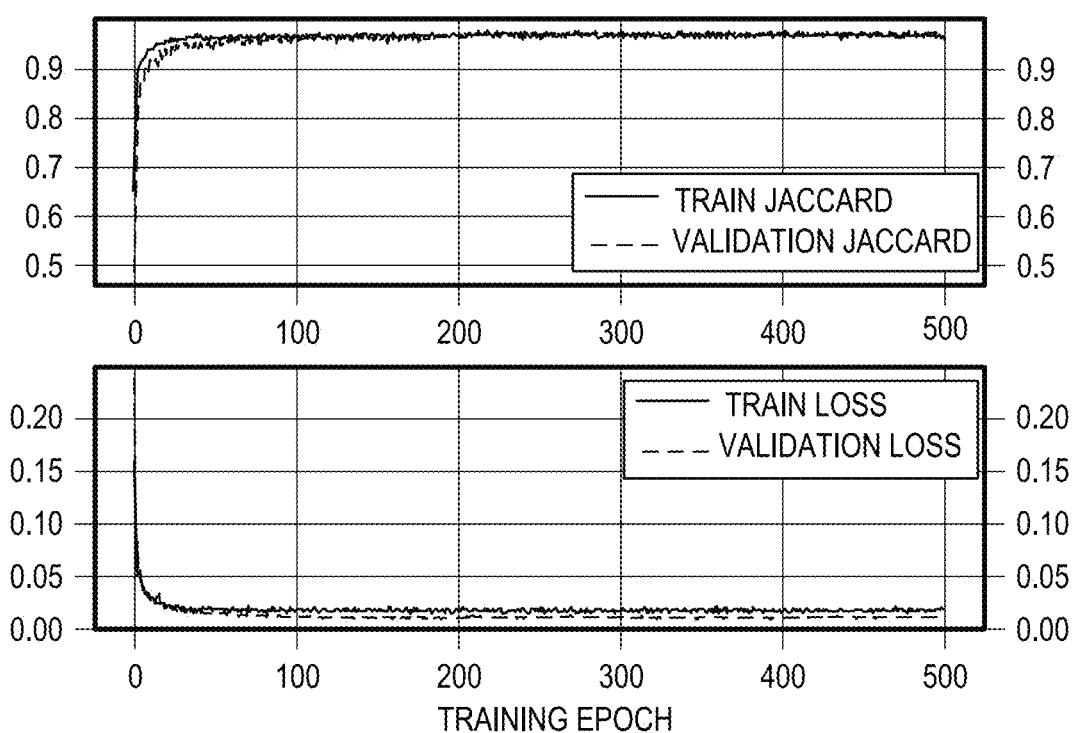
FIG. 8 is an example of the performance of the skin segmentation model.

Referring now to FIG. 8, therein is shown an example of the performance of the skin segmentation model 212 of FIG. 2. The example depicted in FIG. 8 represents the validation accuracy of the skin segmentation model 212 that was trained for 500 epochs with 800 images in each epoch, about 80% data set is reserved for training set and the rest for validation. To measure the accuracy of the skin segmentation model 212, Jaccard score is utilized as expressed in Equation 6 and graphed in this figure.

$$J(A,B)=|A\cap B|/A\cup B| \quad \text{Equation 6}$$

Where A is one data set and B is another data set. The Jaccard index, also known as the Jaccard similarity coefficient, is a statistic used for gauging the similarity and diversity of sample sets. Equation 6 can be used to measure the similarity between finite sample sets, it is defined as the ratio of the intersection over the union of the two sets.

The x-axis represents the number of epochs in both the top and bottom graphs. The y-axes on the top graph represents the Jaccard value. The y-axes in the bottom graph represents the loss value.

Regarding the body part segmentation model 214, this model functions to partition of the patient images 114 to multiple semantically consistent regions. Examples of the body regions or the body part segmentation 208 is shown in FIG. 2, such as head and neck, upper limbs (elbow upwards and elbow downwards), feet and soles, hands and palms, lower limbs (shin, thigh), trunk.

The body part segmentation model 214 is trained with diverse styles of images: entire body, with head, without the head, with clothes, and without clothes or underwear. The data sets include part of the body images or close-up images. The variety of the patient images 114 in data set produces a robust results and the body part segmentation model 214 can correctly predict/segment the body part of a given input image. The data was annotated by annotators. After annotation work, all the data set was double-checked by a test team to make sure that there was no error in the training set. As a specific example, the training data sets include about 5200 images equally distributed between men and women.

As noted earlier, the body part segmentation model 214 utilizes a U-net architecture as an example shown in FIG. 7. The body part segmentation model 214 utilizes a U-net architecture with multi-channel segmentation, each channel segmentation corresponds to a human part to segment. As a specific example and similar to the skin segmentation model 212, the body part segmentation model 214 utilizes a U-net architecture, which includes a specific encoder-decoder scheme. The encoder reduces the spatial dimensions in every layer and increases the channels. On the other hand, the decoder increases the spatial dimensions while reducing the channels. Also as a specific example and similar to the skin segmentation model 212, the body part segmentation model 214 performs scaling by uniformly scales all dimensions of depth, width, and resolution using a compound coefficient.

In addition to the convolution neural network, the body part segmentation model 214 also performs other functions. For example, the body part segmentation model 214 computes the loss functions, the augmentation methods, the voting methods.

Regarding the validation accuracy of the body part segmentation model 214 and as an example, the performance is measured by utilizing a k-fold cross-validation technique to split the training data sets. As a specific example, the data sets are randomly partitioned into 5 equal-sized subsamples. Of the five subsamples, a single subsample is retained as the validation data for testing the body part segmentation model 214, and the remaining 4 subsample is used as training data. Each fold, the body part segmentation model 214 is trained in 300 epochs. In this example, the average Jaccard score is 0:85.

Figure 9:
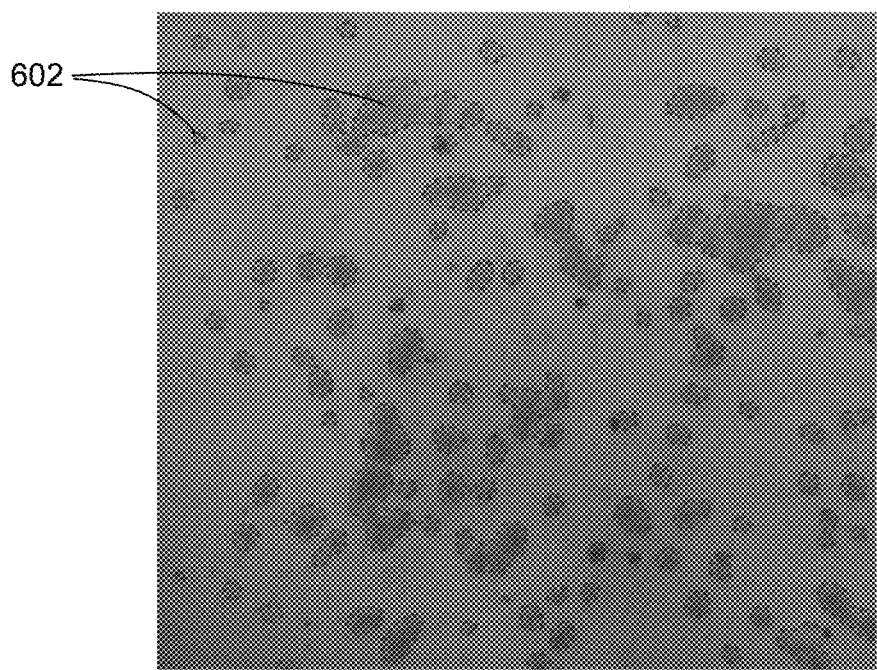
FIG. 9 is an example of an output of the psoriasis segmentation model.

Referring now to FIG. 9, therein is shown an example of an output of the psoriasis segmentation model 220 of FIG. 2. The example shown in FIG. 9 depicts where the psoriasis segmentation model 220 segments or identifies psoriasis regions 602 and ignore the skin part among sick skin region of one of the cropped images 226 of FIG. 2.

The psoriasis segmentation model 220 identifies, segments, and outlines the psoriasis on the skin of the input image, in this flow is one of the cropped images 226. The psoriasis segmentation model 220 can identify different types of psoriasis, such as plaque, guttate, inverse, and pustular, at the same time. The example shown in FIG. 9 shows the psoriasis segmentation model 220 only identifies and outlines the psoriasis regions 602 and excludes all the skin between the psoriasis regions 602.

The psoriasis segmentation model 220 is trained with data sets that include very near shots (lesion detail) to wide shots (full body images). The training data sets include pictures of children and adult and is equally distributed between man and woman in a wide range of skin tones from white to darker skin. Experts annotated a part of the training data set to be gold standards. The rest was done by trained annotators. After the annotation process, the training data set was first double-checked by a test team and then was approved by our experienced board-certified dermatologists. As an augmentation, we use both original images and images covered in the background (non-skin part) by black color.

The psoriasis segmentation model 220 utilizes a binary segmentation approval to the U-net convolution neural network. The psoriasis segmentation model 220 utilizes pretrained model and utilizes transfer learning. The psoriasis segmentation model 220 has the encoder that is pre-trained.

As an example, the psoriasis segmentation model 220 is implemented with U-net model with concatenated steps to connect the encoder and the de-coder part. At the last layer, the psoriasis segmentation model 220 use the Sigmoid activation function as an example of an activation function. As an encoder in our U-Net network, the psoriasis segmentation model 220 again utilizes a convolution neural network that performs scaling by uniformly scales all dimensions of depth, width, and resolution using a compound coefficient. We design our loss function to train this model. Our loss function punishes the model if it does not segment the lesion region or the psoriasis area. This loss function helps the model do very well in complex cases of psoriasis, such as guttate psoriasis.

As a specific example, the psoriasis segmentation model 220 was trained with 200 epochs on 80% of the data sets. The rest of the data sets were used for validation or cross-validation. The psoriasis segmentation model 220 has the performance of 0.73 Jaccard score on the validation data set.

Figure 10:
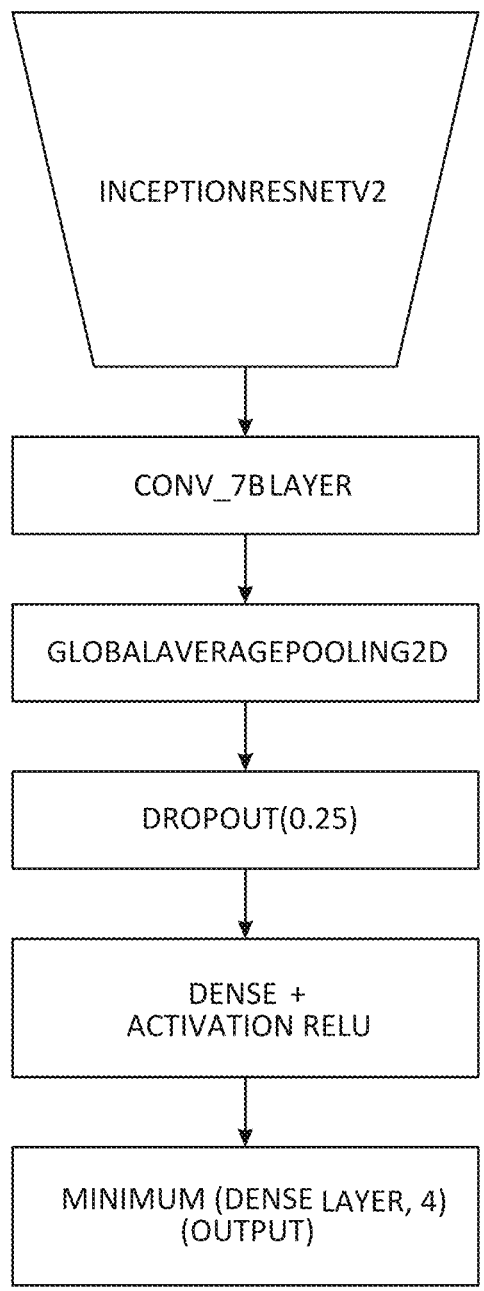
FIG. 10 is an example for a portion of the scoring model.

Referring now to FIG. 10, therein is shown an example for a portion of the scoring model 218 of FIG. 2. The scoring model 218 provides an objective measure of severity based on scores for redness, thickness, and scaliness of a given input image, in this example for each of the cropped images 226. If there is no psoriasis in the input image, such as for each of the cropped images 226, the scoring model 218 will return zero for all three scores as the intermediate scores 210 of FIG. 2.

The scoring model 218 is trained with data sets that include variety in resolution images from a very near shots (detail of lesion) to wide shot (full body images). The training data sets include images of children to older age adults and equally distributed between men and women in wide range of skin tone from white to darker skin.

As specific example, the training data sets include 5844 images, each of which has been annotated three scores: redness, thickness, scaliness. The image sizes vary from 101×227 pixels (a small patch) to 4000×6000 pixels (very high resolution, covering many parts of the body).

A part of the dataset was annotated by experts to be gold standards. Trained annotators did the rest. After the annotation process, the training and cross-validation data sets was double-checked by a test team and then was approved by experienced board-certified dermatologists. As an augmentation, the training and cross-validation data sets include both original images and images covered in the background (nonskin part) by black color.

The scoring model 218 utilizes a regression deep-learning. FIG. 10 depicts a specific example of Inception modules in an Inception ResNet. The scoring model 218 extracts features form input data at varying scales through the utilization of varying convolutional filter sizes together and the Residual technique. As a specific example, the scoring model 218 can be implemented with the residual learning found in He, Kaiming; Zhang, Xiangyu; Ren, Shaoqing; Sun, Jian (2015-12-10)—"Deep Residual Learning for Image Recognition". arXiv: 1512.03385, which is herein incorporated by reference in its entirety.

As a specific example, the scoring model 218 is implemented with transfer learning based on InceptionResnetV2 architecture. The last layer of InceptionResnetV2 (the one aims to predict 1000 classes of 'imagenet' dataset) is omitted and the architecture from the beginning until the convolution block just before last layer labeled 'conv_7b' is kept. The scoring model 218 is implemented by also adding one Global average pooling layer, one Dropout layer with the rate 0.25, one Dense layer (with 4 features and using Relu activation), and the minimum of the output of Dense layer and 4 to ensure the final outputs range from 0 to 4. The weights in the reused layers are used as the initial points for our weights.

Regarding the validation of the scoring model 218, 80/20 for the training and validation set. The mean squared error is used as the loss function. The initial learning rate is 0:0001, after 50 epochs, the mean squared error (MSE) is 0.23 and the L1-metric score is 0.33.

Figure 11:
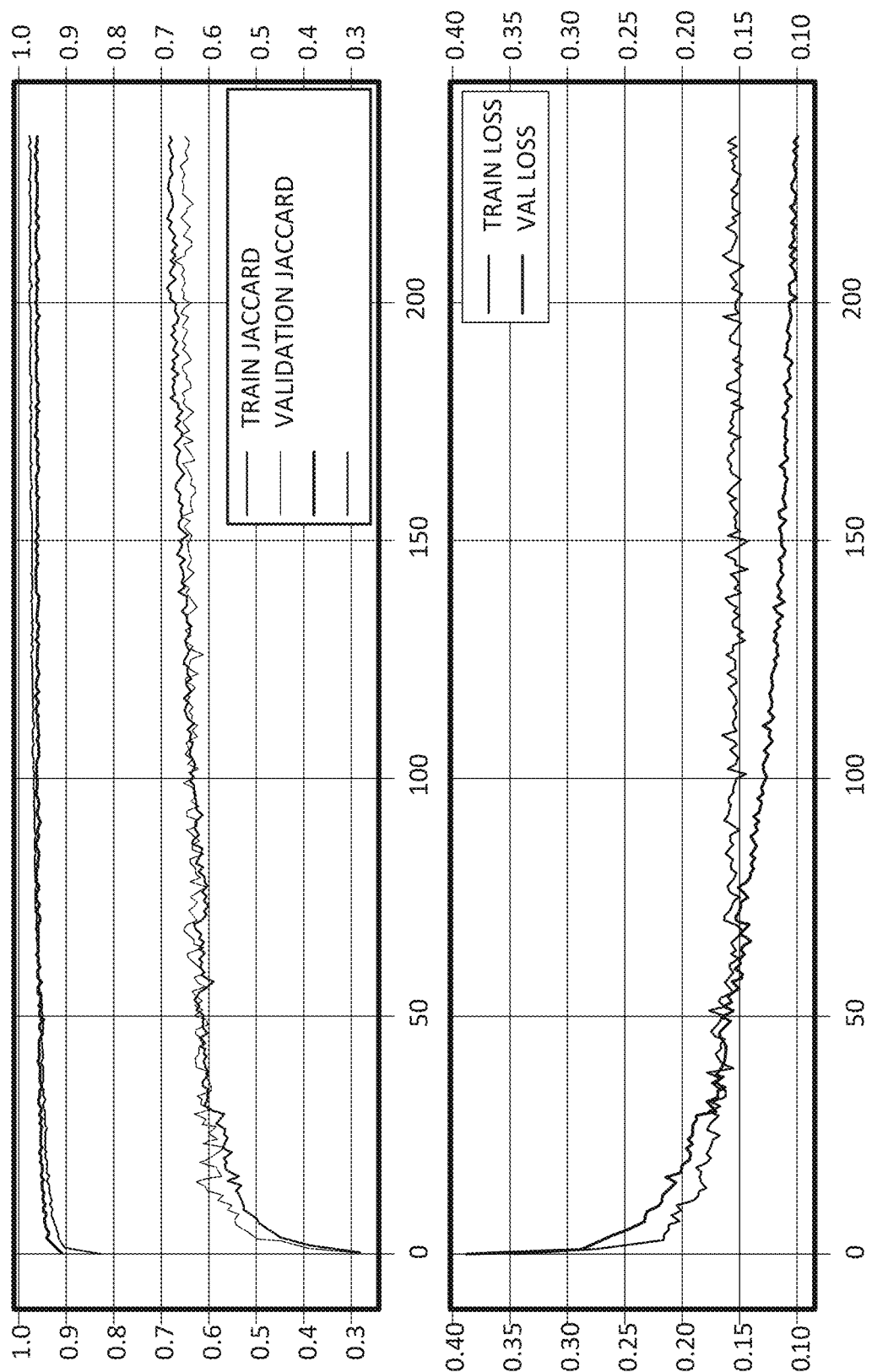
FIG. 11 is an example of the performance of the psoriasis segmentation model.

Referring now to FIG. 11, therein is shown an example of the performance of the psoriasis segmentation model 220 of FIG. 2. The example shown in FIG. 11 represents the accuracy and loss of this model with Jaccard metric.

Figure 12:
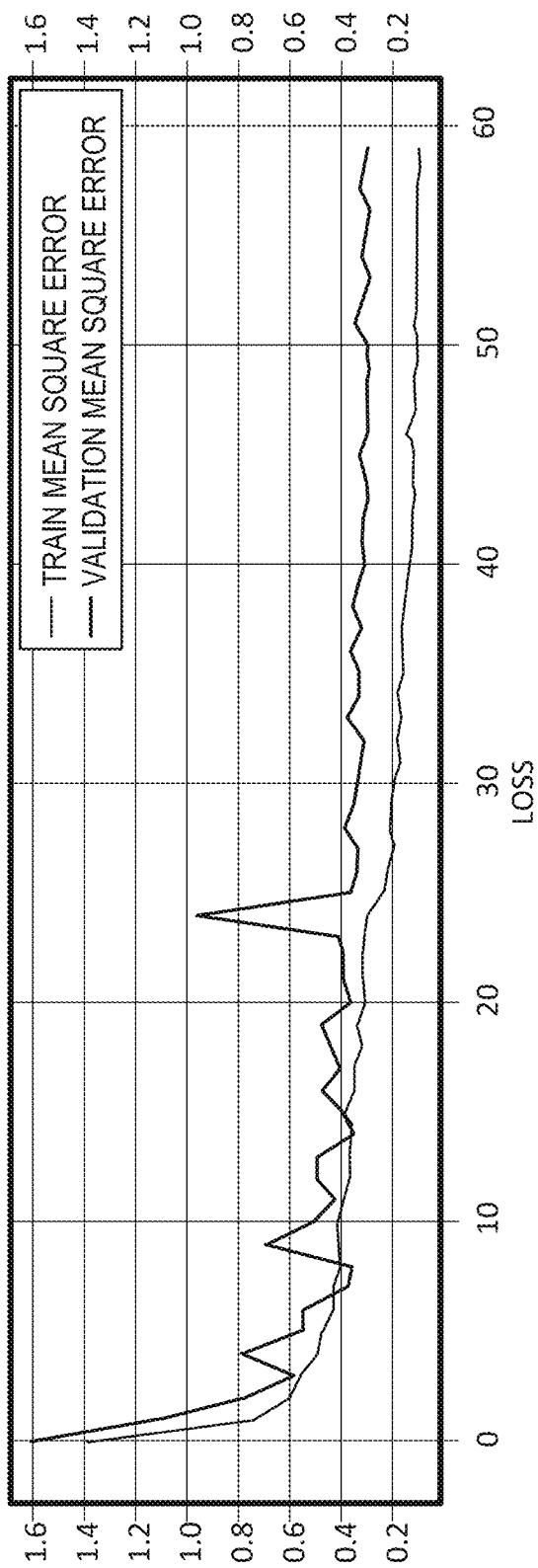
FIG. 12 is an example of the performance of the scoring model.
Figure 12:
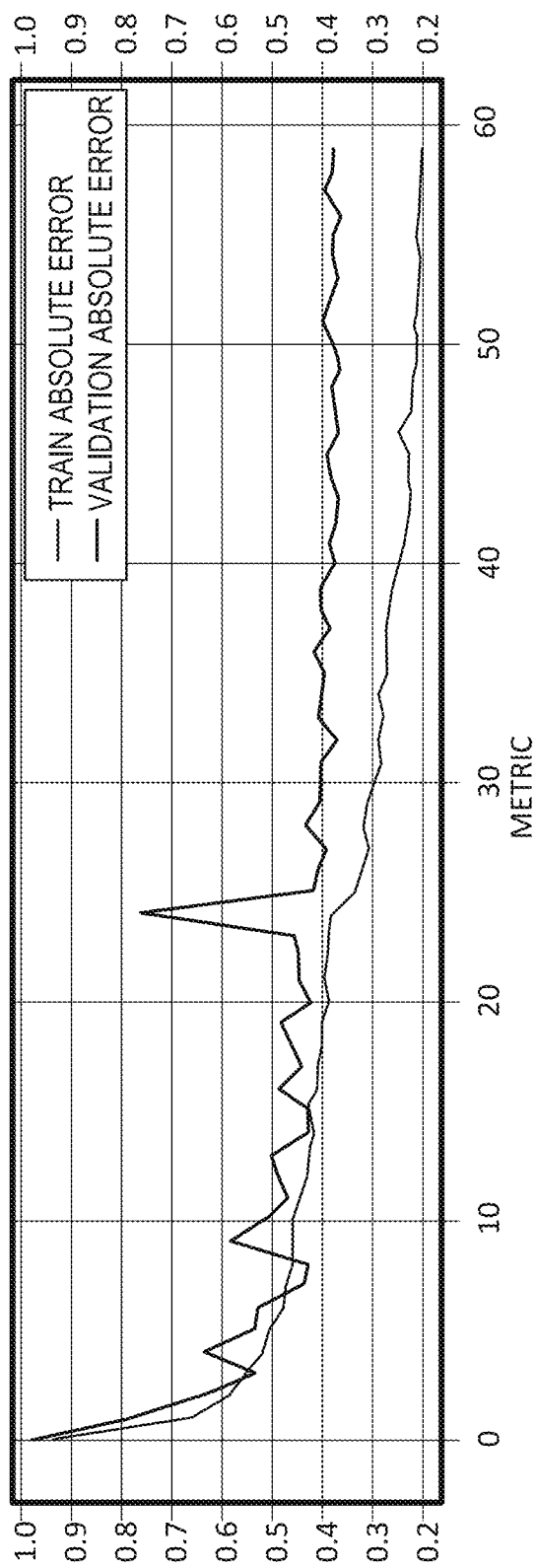

Referring now to FIG. 12, therein is shown an example of the performance of the scoring model 218 of FIG. 2. The example shown in FIG. 12 represents the accuracy and loss of this model with absolute error metric.

Figure 13:
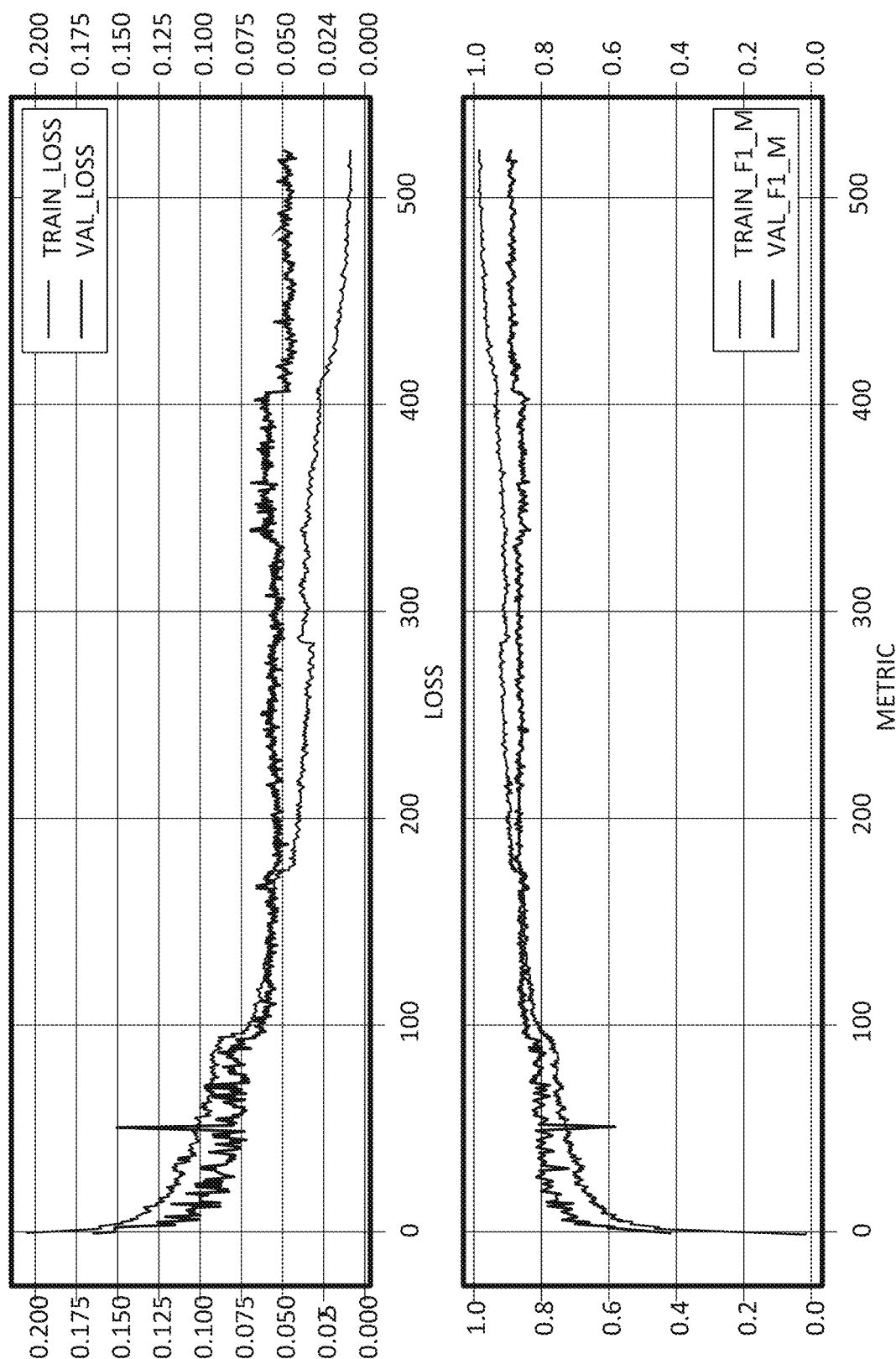
FIG. 13 is an example of the performance of the body part segmentation model.

Referring now to FIG. 13, therein is shown an example of the performance of the body part segmentation model 214 of FIG. 2. The example shown in FIG. 13 the loss and accuracy of the body part segmentation model 214 with F-1 score metric.

Figure 14:
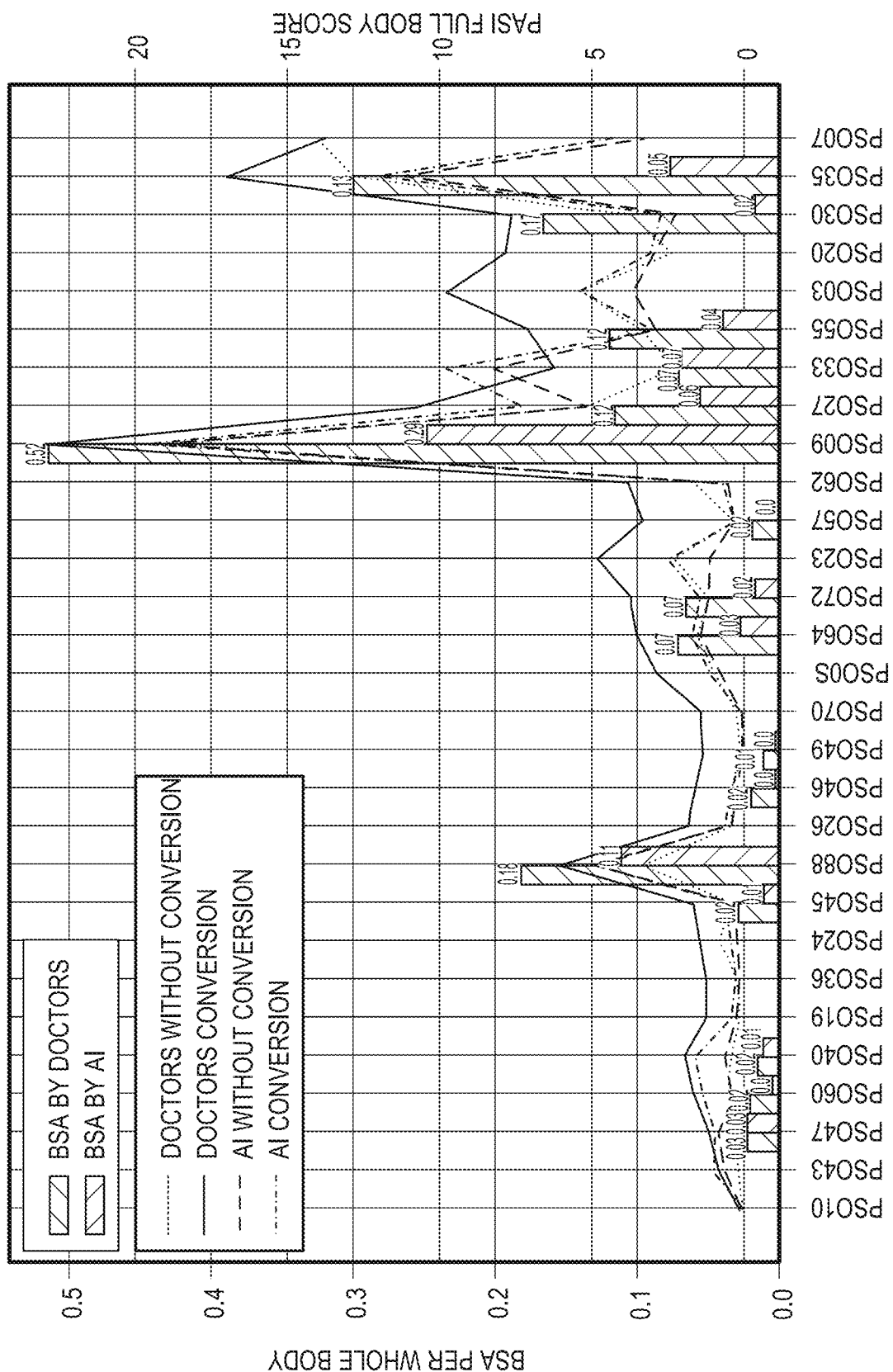
FIG. 14 is an example of the performance comparison of the full body PASI score.

Referring now to FIG. 14, therein is an example of the performance comparison of the full body PASI score 116. In this example shown in FIG. 14, the x-axis represents individual patients. The y-axis on the left-hand side of the graph represent the BSA per whole body of each of the patients along the x-axis. The y-axis on the right-hand side of the graph represents the full-body PASI score 116.

The bar chart depicts the BSA as assessed by the doctor as well as by the compute system 100 with the psoriasis diagnostic mechanism. FIG. 14 depicts that the doctors has a higher value or percentage for the BSA than computed by the compute system 100.

In this example, FIG. 14 also depicts two dashed lines for the full body PASI score 116 without the conversion function (shown as an example in Equation 4) being applied, one based on the doctors determination and one based off the compute system 100. Also in this example, FIG. 14 also depicts two solid lines for the full body PASI score 116 with the conversion function applied, one based on the doctors determination and one based off the compute system 100.

The solid lines and the dotted lines mostly track but there are areas where not only the lines do not track but the values vary more. The non-tracking or larger value difference shows a difference to the full body PASI score 116 between the doctor and the compute system 100 for both with conversion function applied and not applied. This is illustrated Table 3.

TABLE 3

ICC results between score with conversion by doctors and score by compute system

| Type | Description | ICC | CI 95% |
|---|---|---|---|
| ICC1 | Single raters absolute | 0.805877 | [0.63, 0.9] |
| ICC2 | Single random raters | 0.814056 | [0.3, 0.93] |
| ICC3 | Single fixed raters | 0.888966 | [0.78, 0.95] |
| ICC1k | Average raters absolute | 0.892505 | [0.77, 0.95] |
| ICC2k | Average random raters | 0.897498 | [0.46, 0.97] |
| ICC3k | Average fixed raters | 0.941220 | [0.87, 0.97] |

Table 3: ICC results between score with conversion by doctors and score by compute system The intraclass correlation coefficient (ICC) represent agreement between raters. The closer the ICC value is to 1, the stronger the agreement between raters and the closer the ICC value is to 0, the greater the discrepancy. If the ICC greater than or equal to 0:90 indicates excellent agreement, 0:75 to 0:90 good agreement, 0:50 to 0:75 moderate agreement, and ICC<0:50 poor agreement. The confidence interval (CI) of 95% represents the range of ICC values that 95% of values would fall into the range noted in that column.

The ICC values in Table 3 indicate excellent agreement between the compute system 100 and doctors. The CI values are somewhat broad. This can be attributed to the different in the BSA determined by the doctors versus BSA computed by the compute system 100.

Figure 15:
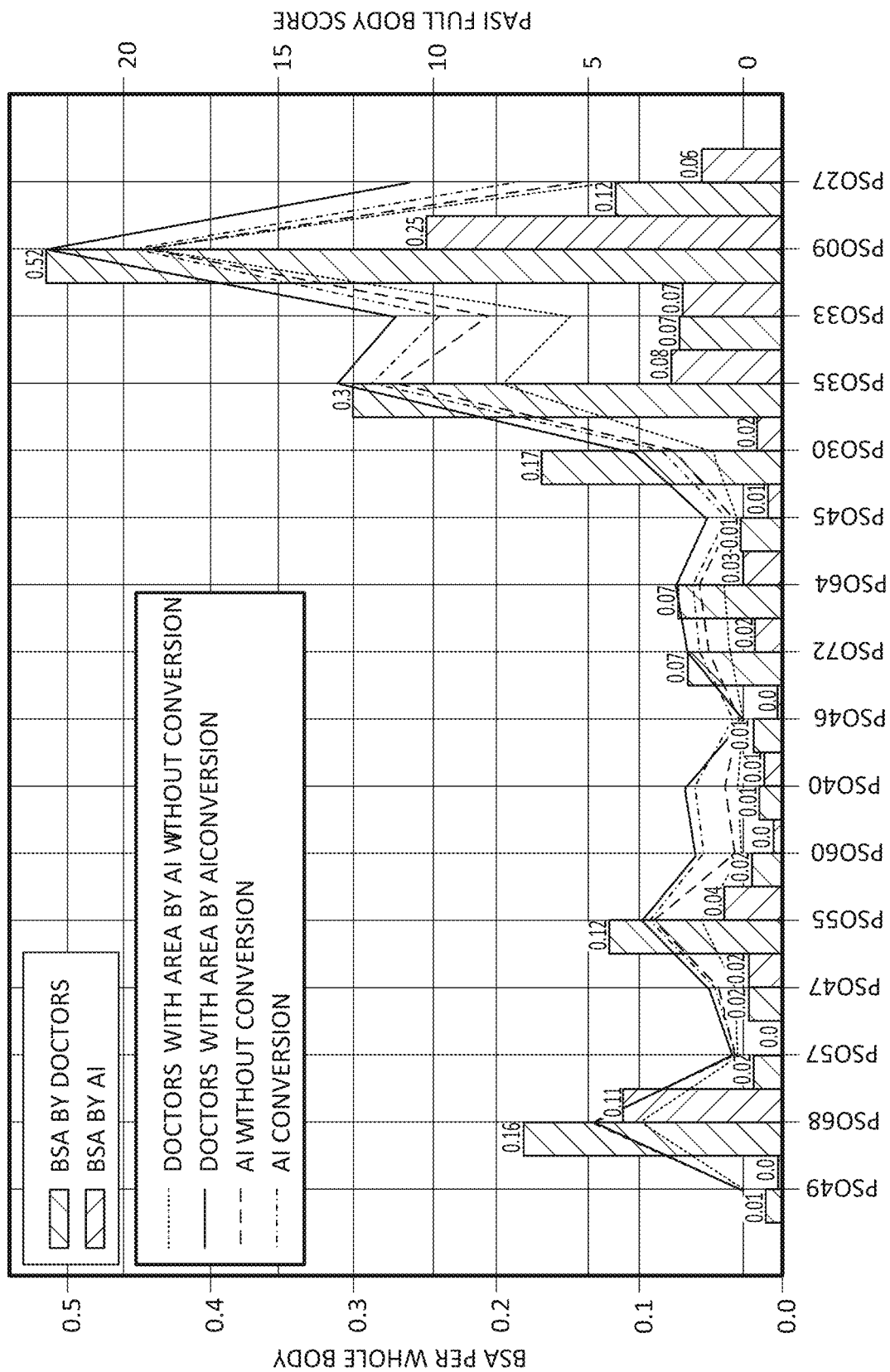
FIG. 15 is an example of the performance comparison with same BSA of the full body PASI score.

Referring now to FIG. 15, therein is shown an example of the performance comparison with same BSA of the full body PASI score 116. In this example shown in FIG. 15, the x-axis represents individual patients. The y-axis on the left-hand side of the graph represent the BSA per whole body of each of the patients along the x-axis. The y-axis on the right-hand side of the graph represents the full-body PASI score *.

The bar chart depicts the BSA as assessed by the doctor as well as by the compute system 100 with the psoriasis diagnostic mechanism. FIG. 14 depicts that the doctors has a higher value or percentage for the BSA than computed by the compute system 100.

In this example, FIG. 14 also depicts two dashed lines for the full body PASI score 116 without the conversion function (shown as an example in Equation 4) being applied, one based of the doctors determination and one based off the compute system 100. Also in this example, FIG. 14 also depicts two solid lines for the full body PASI score 116 with the conversion function applied, one based on the doctor's determination and one based off the compute system 100.

The solid lines and the dotted lines track more closely because the full body PASI score 116 is computed with doctors using the BSA computed by the compute system 100 but still using the scores for redness, thickness, and scaling scores determined by the doctors. This is illustrated Table 4.

TABLE 4

ICC results between score with conversion by doctors and area by compute system and score with conversion by compute system

| Type | Description | ICC | CI 95% |
|---|---|---|---|
| ICC1 | Single raters absolute | 0.976792 | [0.94, 0.99] |
| ICC2 | Single random raters | 0.976874 | [0.9, 0.99] |
| ICC3 | Single fixed raters | 0.983820 | [0.95, 0.99] |
| ICC1k | Average raters absolute | 0.988260 | [0.97, 1.0] |
| ICC2k | Average random raters | 0.988302 | [0.95, 1.0] |
| ICC3k | Average fixed raters | 0.991844 | [0.98, 1.0] |

Table 4: ICC results between score with conversion by doctors and area by compute system and score with conversion by compute system As noted earlier, the closer the ICC value is to 1, the stronger the agreement between raters and the closer the ICC value is to 0, the greater the discrepancy. If the ICC is greater than 0.90, this represents excellent agreement. The confidence interval (CI) of 95% represents the range of ICC values that 95% of values would fall into the range noted in that column.

The ICC values in Table 4 indicate excellent agreement between the compute system 100 and doctors. However, not only are the ICC very close to 1, the CI 95% is all at or mostly above 0.9 and a tighter range of values. This remarkable improvement can be attributed the same BSA used by both the doctors and by the compute system 100.

The compute system 100 and the embodiments provides an objective, repeatable full body score based on the very high values of ICC as well as a very tight range for the values for CIT 95% and the closeness to the value of 1.0.

The functional units or circuits in the first device 102 can work individually and independently of the other functional units or circuits. The first device 102 can work individually and independently from the network 104, the second device 106, other devices or vehicles, or a combination thereof.

The functional units or circuits described above can be implemented in hardware. For example, one or more of the functional units or circuits can be implemented using a gate, circuitry, a processor, a computer, integrated circuit, integrated circuit cores, a pressure sensor, an inertial sensor, a microelectromechanical system (MEMS), a passive device, a physical non-transitory memory medium containing instructions for performing the software function, a portion therein, or a combination thereof.

Figure 16:
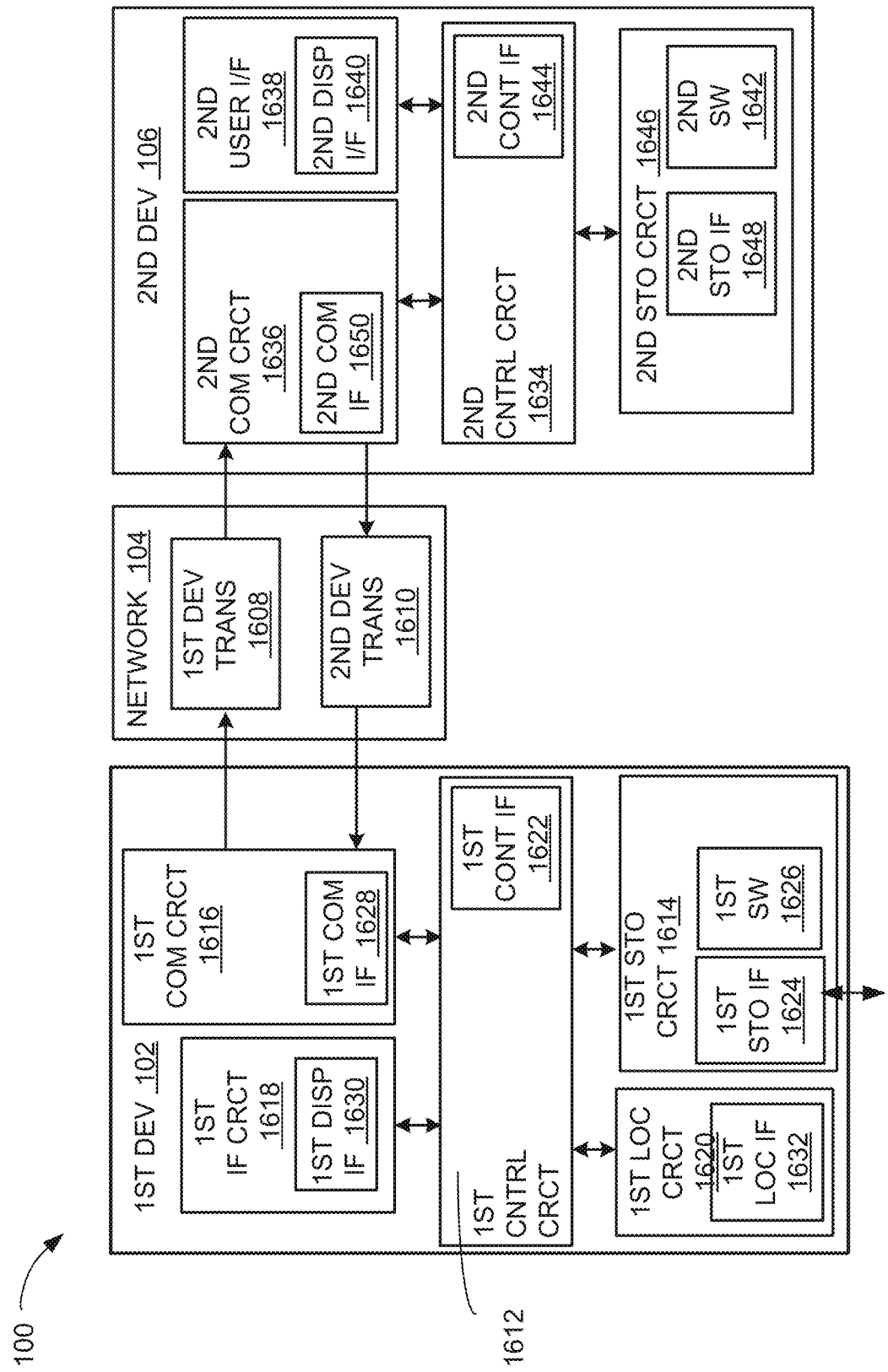
FIG. 16 is an exemplary block diagram of the compute system in an embodiment.

Referring now to FIG. 16, therein is shown an exemplary block diagram of the compute system 100 in an embodiment. The compute system 100 can include the first device 102, the network 104, and the second device 106. The first device 102 can send information in a first device transmission 1608 over the network 104 to the second device 106. The second device 106 can send information in a second device transmission 1610 over the network 104 to the first device 102 or the vehicle 201 of FIG. 2.

For illustrative purposes, the compute system 100 is shown with the first device 102 as a client device, although it is understood that the compute system 100 can include the first device 102 as a different type of device.

Also, for illustrative purposes, the compute system 100 is shown with the second device 106 as a server, although it is understood that the compute system 100 can include the second device 106 as a different type of device. For example, the second device 106 can be a client device. By way of an example, the compute system 100 can be implemented entirely on the first device 102.

Also, for illustrative purposes, the compute system 100 is shown with interaction between the first device 102 and the second device 106. However, it is understood that the first device 102 can be a part of or the entirety of an autonomous vehicle, a smart vehicle, or a combination thereof. Similarly, the second device 106 can similarly interact with the first device 102 representing the autonomous vehicle, the intelligent vehicle, or a combination thereof.

For brevity of description in this embodiment of the present invention, the first device 102 will be described as a client device, the vehicle 201, and the second device 106 will be described as a server device. The embodiment of the present invention is not limited to this selection for the type of devices. The selection is an example of an embodiment of the present invention.

The first device 102 can include a first control circuit 1612, a first storage circuit 1614, a first communication circuit 1616, a first interface circuit 1618, and a first location circuit 1620. The first control circuit 1612 can include a first control interface 1622. The first control circuit 1612 can execute a first software 1626 to provide the intelligence of the compute system 100.

The first control circuit 1612 can be implemented in a number of different manners. For example, the first control circuit 1612 can be a processor, an application specific integrated circuit (ASIC) an embedded processor, a microprocessor, a hardware control logic, a hardware finite state machine (FSM), a digital signal processor (DSP), or a combination thereof. The first control interface 1622 can be used for communication between the first control circuit 1612 and other functional units or circuits in the first device 102. The first control interface 1622 can also be used for communication that is external to the first device 102.

The first control interface 1622 can receive information from the other functional units/circuits or from external sources, or can transmit information to the other functional units/circuits or to external destinations. The external sources and the external destinations refer to sources and destinations external to the first device 102.

The first control interface 1622 can be implemented in different ways and can include different implementations depending on which functional units/circuits or external units/circuits are being interfaced with the first control interface 1622. For example, the first control interface 1622 can be implemented with a pressure sensor, an inertial sensor, a microelectromechanical system (MEMS), optical circuitry, waveguides, wireless circuitry, wireline circuitry, or a combination thereof.

The first storage circuit 1614 can store the first software 1626. The first storage circuit 1614 can also store the relevant information, such as data representing incoming images, data representing previously presented image, sound files, or a combination thereof.

The first storage circuit 1614 can be a volatile memory, a nonvolatile memory, an internal memory, an external memory, or a combination thereof. For example, the first storage circuit 1614 can be a nonvolatile storage such as non-volatile random-access memory (NVRAM), Flash memory, disk storage, or a volatile storage such as static random-access memory (SRAM).

The first storage circuit 1614 can include a first storage interface 1624. The first storage interface 1624 can be used for communication between the first storage circuit 1614 and other functional units or circuits in the first device 102. The first storage interface 1624 can also be used for communication that is external to the first device 102.

The first storage interface 1624 can receive information from the other functional units/circuits or from external sources, or can transmit information to the other functional units/circuits or to external destinations. The external sources and the external destinations refer to sources and destinations external to the first device 102. The first storage interface 1624 can receive input from and source data to the psoriasis diagnostic module 115.

The first storage interface 1624 can include different implementations depending on which functional units/circuits or external units/circuits are being interfaced with the first storage circuit 1614. The first storage interface 1624 can be implemented with technologies and techniques similar to the implementation of the first control interface 1622.

The first communication circuit 1616 can enable external communication to and from the first device 102. For example, the first communication circuit 1616 can permit the first device 102 to communicate with the second device 106 and the network 104.

The first communication circuit 1616 can also function as a communication hub allowing the first device 102 to function as part of the network 104 and not limited to be an endpoint or terminal circuit to the network 104. The first communication circuit 1616 can include active and passive components, such as microelectronics or an antenna, for interaction with the network 104.

The first communication circuit 1616 can include a first communication interface 1628. The first communication interface 1628 can be used for communication between the first communication circuit 1616 and other functional units or circuits in the first device 102. The first communication interface 1628 can receive information from the second device 106 for distribution to the other functional units/circuits or can transmit information to the other functional units or circuits.

The first communication interface 1628 can include different implementations depending on which functional units or circuits are being interfaced with the first communication circuit 1616. The first communication interface 1628 can be implemented with technologies and techniques similar to the implementation of the first control interface 1622.

The first interface circuit 1618 allows the user 112 of FIG. 1 to interface and interact with the first device 102. The first interface circuit 1618 can include an input device and an output device. Examples of the input device of the first interface circuit 1618 can include a keypad, a touchpad, soft-keys, a keyboard, a microphone, an infrared sensor for receiving remote signals, or any combination thereof to provide data and communication inputs.

The first interface circuit 1618 can include a first display interface 1630. The first display interface 1630 can include an output device. The first display interface 1630 can include a projector, a video screen, a touch screen, a speaker, a microphone, a keyboard, and combinations thereof.

The first control circuit 1612 can operate the first interface circuit 1618 to display information generated by the compute system 100 and receive input from the user 112. The first control circuit 1612 can also execute the first software 1626 for the other functions of the compute system 100, including receiving location information from the first location circuit 1620. The first control circuit 1612 can further execute the first software 1626 for interaction with the network 104 via the first communication circuit 1616. The first control circuit 1612 can operate the psoriasis diagnostic mechanism 115 of FIG. 1.

The first control circuit 1612 can also receive location information from the first location circuit 1620. The first control circuit 1612 can operate the psoriasis diagnostic module 115.

The first location circuit 1620 can be implemented in many ways. For example, the first location circuit 1620 can function as at least a part of the global positioning system, an inertial compute system, a cellular-tower location system, a gyroscope, or any combination thereof. Also, for example, the first location circuit 1620 can utilize components such as an accelerometer, gyroscope, or global positioning system (GPS) receiver.

The first location circuit 1620 can include a first location interface 1632. The first location interface 1632 can be used for communication between the first location circuit 1620 and other functional units or circuits in the first device 102, including the environmental sensors 210.

The first location interface 1632 can receive information from the other functional units/circuits or from external sources, or can transmit information to the other functional units/circuits or to external destinations. The external sources and the external destinations refer to sources and destinations external to the first device 102. The first location interface 1632 can receive the global positioning location from the global positioning system (not shown).

The first location interface 1632 can include different implementations depending on which functional units/circuits or external units/circuits are being interfaced with the first location circuit 1620. The first location interface 1632 can be implemented with technologies and techniques similar to the implementation of the first control circuit 1612.

The second device 106 can be optimized for implementing an embodiment of the present invention in a multiple device embodiment with the first device 102. The second device 106 can provide the additional or higher performance processing power compared to the first device 102. The second device 106 can include a second control circuit 1634, a second communication circuit 1636, a second user interface 1638, and a second storage circuit 1646.

The second user interface 1638 allows an operator (not shown) to interface and interact with the second device 106. The second user interface 1638 can include an input device and an output device. Examples of the input device of the second user interface 1638 can include a keypad, a touchpad, soft-keys, a keyboard, a microphone, or any combination thereof to provide data and communication inputs. Examples of the output device of the second user interface 1638 can include a second display interface 1640. The second display interface 1640 can include a display, a projector, a video screen, a speaker, or any combination thereof.

The second control circuit 1634 can execute a second software 1642 to provide the intelligence of the second device 106 of the compute system 100. The second software 1642 can operate in conjunction with the first software 1626. The second control circuit 1634 can provide additional performance compared to the first control circuit 1612.

The second control circuit 1634 can operate the second user interface 1638 to display information. The second control circuit 1634 can also execute the second software 1642 for the other functions of the compute system 100, including operating the second communication circuit 1636 to communicate with the first device 102 over the network 104.

The second control circuit 1634 can be implemented in a number of different manners. For example, the second control circuit 1634 can be a processor, an embedded processor, a microprocessor, hardware control logic, a hardware finite state machine (FSM), a digital signal processor (DSP), or a combination thereof.

The second control circuit 1634 can include a second control interface 1644. The second control interface 1644 can be used for communication between the second control circuit 1634 and other functional units or circuits in the second device 106. The second control interface 1644 can also be used for communication that is external to the second device 106.

The second control interface 1644 can receive information from the other functional units/circuits or from external sources, or can transmit information to the other functional units/circuits or to external destinations. The external sources and the external destinations refer to sources and destinations external to the second device 106.

The second control interface 1644 can be implemented in different ways and can include different implementations depending on which functional units/circuits or external units/circuits are being interfaced with the second control interface 1644. For example, the second control interface 1644 can be implemented with a pressure sensor, an inertial sensor, a microelectromechanical system (MEMS), optical circuitry, waveguides, wireless circuitry, wireline circuitry, or a combination thereof.

The second storage circuit 1646 can store the second software 1642. The second storage circuit 1646 can also store the information such as data representing incoming images, data representing previously presented image, sound files, or a combination thereof. The second storage circuit 1646 can be sized to provide the additional storage capacity to supplement the first storage circuit 1614.

For illustrative purposes, the second storage circuit 1646 is shown as a single element, although it is understood that the second storage circuit 1646 can be a distribution of storage elements. Also, for illustrative purposes, the compute system 100 is shown with the second storage circuit 1646 as a single hierarchy storage system, although it is understood that the compute system 100 can include the second storage circuit 1646 in a different configuration. For example, the second storage circuit 1646 can be formed with different storage technologies forming a memory hierarchal system including different levels of caching, main memory, rotating media, or off-line storage.

The second storage circuit 1646 can be a controller of a volatile memory, a nonvolatile memory, an internal memory, an external memory, or a combination thereof. For example, the second storage circuit 1646 can be a controller of a nonvolatile storage such as non-volatile random-access memory (NVRAM), Flash memory, disk storage, or a volatile storage such as static random access memory (SRAM).

The second storage interface 1648 can receive information from the other functional units/circuits or from external sources, or can transmit information to the other functional units/circuits or to external destinations. The external sources and the external destinations refer to sources and destinations external to the second device 106.

The second storage interface 1648 can include different implementations depending on which functional units/circuits or external units/circuits are being interfaced with the second storage circuit 1646. The second storage interface 1648 can be implemented with technologies and techniques similar to the implementation of the second control interface 1644.

The second communication circuit 1636 can enable external communication to and from the second device 106. For example, the second communication circuit 1636 can permit the second device 106 to communicate with the first device 102 over the network 104.

The second communication circuit 1636 can also function as a communication hub allowing the second device 106 to function as part of the network 104 and not limited to be an endpoint or terminal unit or circuit to the network 104. The second communication circuit 1636 can include active and passive components, such as microelectronics or an antenna, for interaction with the network 104.

The second communication circuit 1636 can include a second communication interface 1650. The second communication interface 1650 can be used for communication between the second communication circuit 1636 and other functional units or circuits in the second device 106. The second communication interface 1650 can receive information from the other functional units/circuits or can transmit information to the other functional units or circuits.

The second communication interface 1650 can include different implementations depending on which functional units or circuits are being interfaced with the second communication circuit 1636. The second communication interface 1650 can be implemented with technologies and techniques similar to the implementation of the second control interface 1644.

The second communication circuit 1636 can couple with the network 104 to send information to the first device 102. The first device 102 can receive information in the first communication circuit 1616 from the second device transmission 1610 of the network 104. The compute system 100 can be executed by the first control circuit 1612, the second control circuit 1634, or a combination thereof. For illustrative purposes, the second device 106 is shown with the partition containing the second user interface 1638, the second storage circuit 1646, the second control circuit 1634, and the second communication circuit 1636, although it is understood that the second device 106 can include a different partition. For example, the second software 1642 can be partitioned differently such that some or all of its function can be in the second control circuit 1634 and the second communication circuit 1636. Also, the second device 106 can include other functional units or circuits not shown in FIG. 16 for clarity.

The functional units or circuits in the first device 102 can work individually and independently of the other functional units or circuits. The first device 102 can work individually and independently from the second device 106 and the network 104.

The functional units or circuits in the second device 106 can work individually and independently of the other functional units or circuits. The second device 106 can work individually and independently from the first device 102 and the network 104.

The functional units or circuits described above can be implemented in hardware. For example, one or more of the functional units or circuits can be implemented using a gate array, an application specific integrated circuit (ASIC), circuitry, a processor, a computer, integrated circuit, integrated circuit cores, a pressure sensor, an inertial sensor, a microelectromechanical system (MEMS), a passive device, a physical non-transitory memory medium containing instructions for performing the software function, a portion therein, or a combination thereof.

For illustrative purposes, the compute system 100 is described by operation of the first device 102 and the second device 106. It is understood that the first device 102 and the second device 106 can operate any of the modules and functions of the compute system 100.

Figure 17:
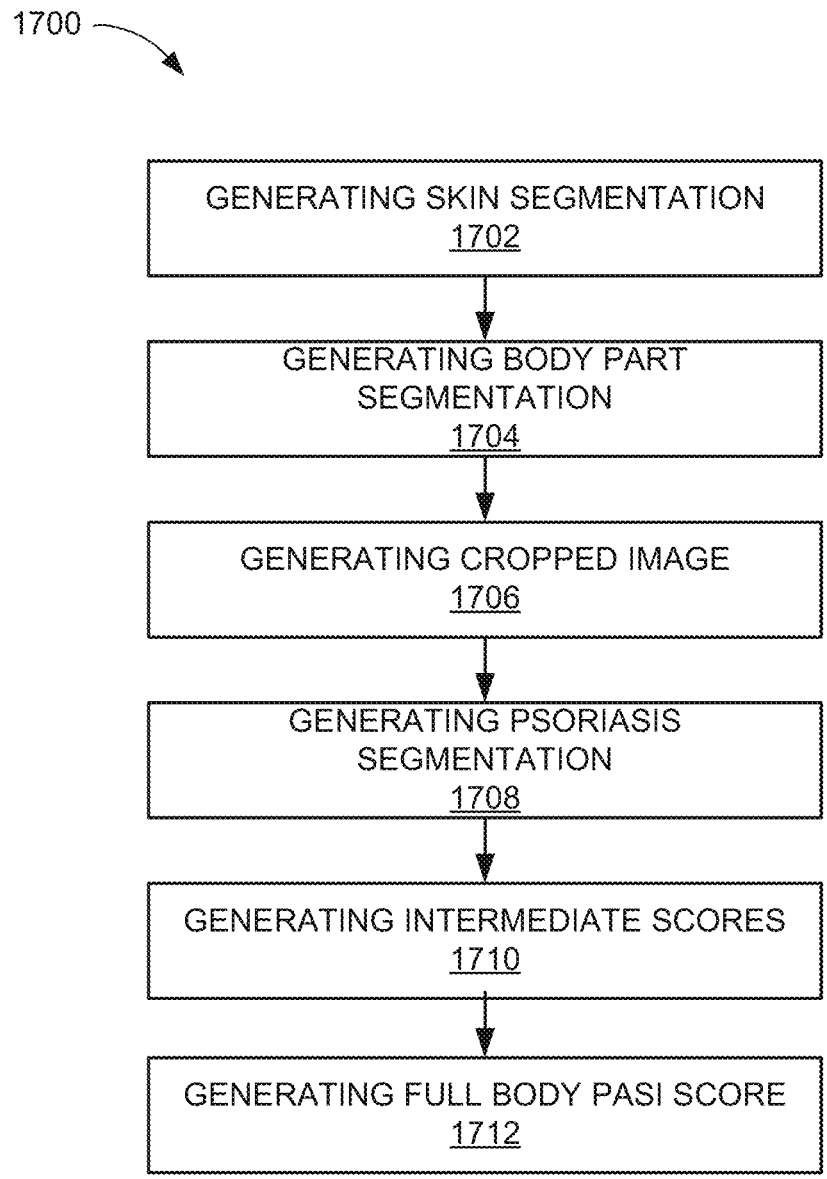
FIG. 17 is a flow chart of a method of operation of a compute system in an embodiment of the present invention.

Referring now to FIG. 17, therein is shown a flow chart of a method 1400 of operation of a compute system 100 of FIG. 1 in an embodiment of the present invention. The method 1700 includes: generating a skin segmentation including a non-skin region and a skin prediction based on a patient image in a block 1702; generating a body part segmentation based on the patient image in a block 1704; generating a cropped image based on the skin segmentation and the body part segmentation with the cropped image includes the non-skin region based on the skin prediction in a block 1706; generating a psoriasis segmentation based on the cropped image and the skin prediction in a block 1708; generating intermediate scores for erythema, induration, desquamation for the cropped image in a block 1710; and generating a full body PASI score based a psoriasis segmentation and the intermediate scores on the for displaying on a device to assist in diagnosis in a block 1712.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of an embodiment of the present invention is that it valuably supports and services the historical trend of reducing costs, simplifying systems, and increasing performance.

These and other valuable aspects of an embodiment of the present invention consequently further the state of the technology to at least the next level.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A method of operation of a compute system comprising:
   generating a skin segmentation including a non-skin region and a skin prediction based on a patient image;
   generating a body part segmentation based on the patient image;
   generating a cropped image based on the skin segmentation and the body part segmentation with the cropped image including the non-skin region based on the skin prediction;
   generating a psoriasis segmentation based on the cropped image and the skin prediction;
   generating intermediate scores for erythema, induration, and desquamation for the cropped image; and
   generating a full body PASI score abased on the psoriasis segmentation and the intermediate scores for displaying on a device to assist in diagnosis.

2. The method as claimed in claim 1 further compromising accepting the patient image based on calculating, for the patient image, a non-skin score less than or equal to non-nominal threshold.

3. The method as claimed in claim 1 further compromising accepting the patient image based on calculating, for the patient image, a nominal metric greater than a nominal threshold.

4. The method as claimed in claim 1 further comprising accepting the patient image based on calculating, for the patient image, a blurry metric, a bad luminosity metric, or a combination thereof less than or equal to a blurry threshold, a bad luminosity threshold, respectively, or a combination thereof.

5. The method as claimed in claim 1 wherein:
generating the cropped image includes generating one or more cropped images; and
generating the full body PASI score includes aggregating the psoriasis segmentation and the intermediate scores for each of the cropped images.

6. The method as claimed in claim 1 wherein generating the full body PASI score include applying a conversion function to the psoriasis segmentation for the cropped image.

7. The method as claimed in claim 1 further comprising checking a quality criteria for the patent image to meet or exceed a quality threshold prior to processing for the full body PASI score.

8. A compute system comprising:
a control circuit, including a processor, configured to:
generate a skin segmentation including a non-skin region and a skin prediction based on a patient image,
generate a body part segmentation based on the patient image,
generate a cropped image based on the skin segmentation and the body part segmentation with the cropped image includes the non-skin region based on the skin prediction,
generate a psoriasis segmentation based on the cropped image and the skin prediction,
generate intermediate scores for erythema, induration, and desquamation for the cropped image, and
generate a full body PASI score based on the psoriasis segmentation and the intermediate scores for displaying on a device to assist in diagnosis.

9. The system as claimed in claim 8 wherein the control circuit is further configured to accept the patient image based on calculating, for the patient image, a non-skin score less than or equal to non-nominal threshold.

10. The system as claimed in claim 8 wherein the control circuit is further configured to accept the patient image based on calculating, for the patient image, a nominal metric greater than a nominal threshold.

11. The system as claimed in claim 8 wherein the control circuit is further configured to accept the patient image based on calculating, for the patient image, a blurry metric, a bad luminosity metric, or a combination thereof less than or equal to a blurry threshold, a bad luminosity threshold, respectively, or a combination thereof.

12. The system as claimed in claim 8 wherein the control circuit is further configured to:
generate the cropped image including generate one or more cropped images; and
generate the full body PASI score including aggregate the psoriasis segmentation and the intermediate scores for each of the cropped images.

13. The system as claimed in claim 8 wherein the control circuit is further configured to generate the full body PASI score including apply a conversion function to the psoriasis segmentation for the cropped image.

14. The system as claimed in claim 8 wherein the control circuit is further configured to check a quality criteria for the patent image to meet or exceed a quality threshold prior to processing for the full body PASI score.

15. A non-transitory computer readable medium including instructions for a compute system comprising:
generating a skin segmentation including a non-skin region and a skin prediction based on a patient image;
generating a body part segmentation based on the patient image;
generating a cropped image based on the skin segmentation and the body part segmentation with the cropped image including the non-skin region based on the skin prediction;
generating a psoriasis segmentation based on the cropped image and the skin prediction;
generating intermediate scores for erythema, induration, and desquamation for the cropped image; and
generating a full body PASI score based on the psoriasis segmentation and the intermediate scores for displaying on a device to assist in diagnosis.

16. The non-transitory computer readable medium as claimed in claim 15 further compromising accepting the patient image based on calculating, for the patient image, a non-skin score less than or equal to non-nominal threshold.

17. The non-transitory computer readable medium as claimed in claim 15 further compromising accepting the patient image based on calculating, for the patient image, a nominal metric greater than a nominal threshold.

18. The non-transitory computer readable medium as claimed in claim 15 further compromising accepting the patient image based on calculating, for the patient image, a blurry metric, a bad luminosity metric, or a combination thereof less than or equal to a blurry threshold, a bad luminosity threshold, respectively, or a combination thereof.

19. The non-transitory computer readable medium as claimed in claim 15 wherein:
generating the cropped image includes generating or more cropped images; and
generating the full body PASI score includes aggregating the psoriasis segmentation and the intermediate scores for each of the cropped images.

20. The non-transitory computer readable medium as claimed in claim 15 wherein generating the full body PASI score include applying a conversion function to the psoriasis segmentation for the cropped image.

* * * * *

UNITED STATES PATENT AND TRADEMARK OFFICE
CERTIFICATE OF CORRECTION

PATENT NO. : 11,890,105 B1
APPLICATION NO. : 17/893632
DATED : February 6, 2024
INVENTOR(S) : Tien Dung Nguyen et al.

It is certified that error appears in the above-identified patent and that said Letters Patent is hereby corrected as shown below:

In the Claims

Column 30, Claim 1, Line 57, delete "generating a full body PASI score abased on the psoriasis" and insert therefor --generating a full body PASI score based on the psoriasis--

Column 32, Claim 19, Line 45, delete "generating the cropped image includes generating or more" and insert therefor --generating the cropped image includes generating one or more--

Signed and Sealed this
Twenty-sixth Day of March, 2024

*Katherine Kelly Vidal*
Katherine Kelly Vidal
*Director of the United States Patent and Trademark Office*